United States Patent
Hebach et al.

(10) Patent No.: US 9,670,193 B2
(45) Date of Patent: Jun. 6, 2017

(54) TRIFLUOROMETHYL-OXADIAZOLE DERIVATIVES AND THEIR USE IN THE TREATMENT OF DISEASE

(71) Applicants: Christina Hebach, Muenchenstein (DE); Joerg Kallen, Basel (CH); Joachim Nozulak, Heitersheim (DE); Marina Tintelnot-Blomley, Maulburg (DE); Leo Widler, Muenchenstein (CH)

(72) Inventors: Christina Hebach, Muenchenstein (DE); Joerg Kallen, Basel (CH); Joachim Nozulak, Heitersheim (DE); Marina Tintelnot-Blomley, Maulburg (DE); Leo Widler, Muenchenstein (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/360,013

(22) PCT Filed: Nov. 26, 2012

(86) PCT No.: PCT/IB2012/056739
§ 371 (c)(1),
(2) Date: May 22, 2014

(87) PCT Pub. No.: WO2013/080120
PCT Pub. Date: Jun. 6, 2013

(65) Prior Publication Data
US 2014/0329825 A1 Nov. 6, 2014

Related U.S. Application Data
(60) Provisional application No. 61/564,031, filed on Nov. 28, 2011.

(51) Int. Cl.
| | |
|---|---|
| *A61K 31/4245* | (2006.01) |
| *C07D 413/04* | (2006.01) |
| *C07D 413/14* | (2006.01) |
| *A61K 31/4439* | (2006.01) |
| *A61K 31/444* | (2006.01) |
| *A61K 31/497* | (2006.01) |
| *A61K 31/506* | (2006.01) |

(52) U.S. Cl.
CPC .......... *C07D 413/14* (2013.01); *A61K 31/444* (2013.01); *A61K 31/4439* (2013.01); *A61K 31/497* (2013.01); *A61K 31/506* (2013.01); *C07D 413/04* (2013.01)

(58) Field of Classification Search
CPC .......................... C07D 413/04; C07D 413/14
See application file for complete search history.

(56) References Cited

U.S. PATENT DOCUMENTS

| | | | |
|---|---|---|---|
| 9,056,843 B2 | 6/2015 | Hebach et al. | |
| 2005/0288282 A1 | 12/2005 | Delorme et al. | |
| 2006/0058298 A1 | 3/2006 | Delorme et al. | |

FOREIGN PATENT DOCUMENTS

| | | |
|---|---|---|
| EP | 2729454 B1 | 9/2015 |
| WO | 2005/040152 A1 | 5/2005 |
| WO | 2008/011131 A2 | 1/2008 |
| WO | 2009/019656 A1 | 2/2009 |
| WO | 2009/029632 A1 | 3/2009 |
| WO | 2011/088181 A1 | 7/2011 |
| WO | 2011/088192 A1 | 7/2011 |
| WO | 2012/011592 A1 | 1/2012 |
| WO | 2013/008162 A1 | 1/2013 |

OTHER PUBLICATIONS

Didonna et al. The promise and perils of HDAC inhibitors in neurodegeneration. Annals of Clinical and Translational Neurology, 2015, 2, 79-101.*
Liu et al. Discovery of potent, selective, orally bioavailable stearoyl-CoA desaturase 1 inhibitors. J Med Chem. Jun. 28, 2007;50(13):3086-100.

* cited by examiner

*Primary Examiner* — Brian McDowell
(74) *Attorney, Agent, or Firm* — Shawn D. Britt

(57) ABSTRACT

The invention relates to novel trifluoromethyl-oxadiazole derivatives of formula (I), and pharmaceutically acceptable salts thereof, in which all of the variables are as defined in the specification, pharmaceutical compositions thereof, pharmaceutical combinations thereof, and their use as medicaments, particularly for the treatment of neurodegeneration, muscle atrophy or diabetes/metabolic syndrome via inhibition of HDAC4.

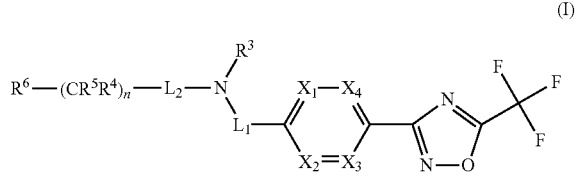

(I)

13 Claims, No Drawings

TRIFLUOROMETHYL-OXADIAZOLE DERIVATIVES AND THEIR USE IN THE TREATMENT OF DISEASE

RELATED APPLICATIONS

This application is a U.S. National Phase filing of International Application No. PCT/IB2012/056,739 filed Nov. 26, 2012, which claims priority to U.S. Application No. 61/564,031 filed Nov. 28, 2011, the contents of which are incorporated herein by reference in their entirety.

FIELD OF THE INVENTION

The invention relates to novel trifluoromethyl-oxadiazole derivatives and pharmaceutically acceptable salts thereof, pharmaceutical compositions thereof, pharmaceutical combinations thereof, and their use as medicaments, particularly for the treatment of neurodegeneration, muscle atrophy or diabetes/metabolic syndrome via inhibition of HDAC4.

BACKGROUND OF THE INVENTION

Huntington's disease (HD) is an autosomal dominant neurodegenerative disease with an incidence of 1 in 10'000 (approx. 30'000 patients in USA). HD is not prevalent to any particular population, race or ethnic group, and both genders are affected. HD manifests in middle age (30-50 years) with jerking, uncontrollable movement of the limbs, trunk and face followed by progressive loss of mental abilities and development of psychiatric problems. The disease continues without remission over 10 to 25 years and is ultimately terminal.

The cause of the disease is an expansion of CAG repeats in exon 1 of the gene coding for the protein huntingtin. This expansion produces a mutated protein (mHTT) with a polyglutamine repeat within the amino terminus. mHTT and its proteolytic N-terminal fragments accumulate in intracellular aggregates and have been shown to interfere with the transcriptional machinery of the cell.

Transcriptional dysregulation is the first detectable change in HD and it is observed in both human and animal correlates of disease. Modulation of transcriptional activity can be achieved via the inhibition of histone deacetylase enzymes a family of 11 isotypes further classified into sub-families: HDAC1,2,3,8 (Class I); HDAC4,5,7,9 (Class IIa), HDAC6,10 (Class IIb) and HDAC11 (Class IV). HDAC inhibition can restore the balance and a pan-HDAC inhibitor (SAHA) has been found efficacious in *Drosophila* and mouse assays for Huntington's pathology (Hockly et al., PNAS (2003) 100:2041; Kazantsev A G, Thompson L M., Nat Rev Drug Discov. (2008) 7:854-68). As SAHA is a non-selective inhibitor of all HDACs Class I, IIa+IIb and IV sub-families it is not possible to determine through which isotype/sub-family the beneficial effects are mediated.

Recently the individual role of members of the Class IIa sub-family (HDAC4,5,7,9) was investigated by knockingdown the respective isotypes by genetic crossing with the R6/2 mouse, a genetically engineered mouse mimicking the human HD pathology (Mielcarek M. et al., J. Neurology, Neurosurgery and Psychiatry (2009) 79:A8). The resulting double transgenic mice strains for which HDAC 5, HDAC 7 or HDAC 9 were knocked-down did not show any improvement of the R6/2 phenotype whereas the reduction in HDAC4 expression levels improved the motor impairment phenotype of the R6/2 mice.

HDAC4 inhibition therefore provides a potential opportunity for pharmaceutical intervention and treatment of Huntington's disease.

Class IIa HDACs are also expressed in skeletal muscle and are expressed at a lower level in slow-twitching muscle compared to fast-twitching muscle. Deletion of any combination of four alleles of HDAC4, 5 and 9 leads to more slow-fiber gene expression, which in turn leads to enhanced running endurance (Potthoff et al., J. Clin. Invest. (2007) 117, 2459-2467). Furthermore, HDAC4 gene expression is highly upregulated in muscle after denervation (Bodine et al., Science (2001) 294, 1704-1708). HDAC4 inhibits the expression of FGFBP1, which interacts with FGF7/10/22 and promotes reinnervation (Williams et al., Science (2009) 326, 1549-1554). Upon denervation, increased HDAC4 expression also represses the expression of Dach2, which in turn leads to increased expression of myogenin. Myogenin upregulates the expression of the two E3 ubiquitin ligases that are required for muscle atrophy. Denervated mice lacking HDAC4 (muscle specific knockout) or HDAC5 demonstrated a 30% loss in muscle weight compared to the 50% loss of muscle mass in WT mice, while mice lacking both HDAC4 and HDAC5 demonstrated only a 10% decrease in muscle weight (Moresi et al., Cell (2010) 143, 35-45).

Inhibition of HDAC4 thus also provides a potential method for treating muscle atrophy.

In addition, a very recent publication has shown a pivotal role for HDAC Class IIa in the regulation of glucose homeostasis (Mihaylova M M, et al., Cell (2011) 145, 607-21). In a mouse model for hyperglycemia (ob/ob mouse) reduction of Class IIa HDACs using shRNAs against HDAC4, 5 and 7 has been shown to lower blood glucose and increase glycogen storage. Furthermore, reduction of Class IIa HDACs in a mouse model for type 2 diabetes (high fat diet mouse) significantly improves hyperglycemia.

Use of a pharmacological agent to reduce the activity of HDAC4 may therefore also provide a useful therapeutic intervention for the treatment of diabetes/metabolic syndrome.

The present invention relates to novel trifluoromethyloxadiazole derivatives having selective HDAC4 inhibitory activity and their medical use, particularly in the treatment of Huntington's disease, muscle atrophy and diabetes/metabolic syndrome.

SUMMARY OF THE INVENTION

In a first aspect of the invention, there is therefore provided a compound of formula (I), or a pharmaceutically acceptable salt thereof,

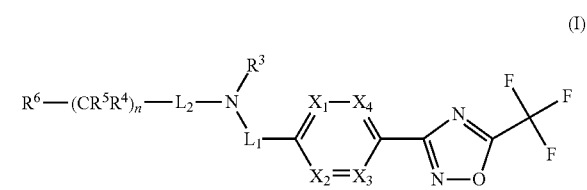

wherein
$X_1$ represents N or $CR^1$;
$X_2$ represents N or $CR^2$;
$X_3$ represents N or CH;

$X_4$ represents N or CH;
and wherein at least one of $X_1$, $X_2$, $X_3$ and $X_4$ is N and not more than two of $X_1$, $X_2$, $X_3$ and $X_4$ are N;
$R^1$ and $R^2$ independently represent hydrogen, chloro or $C_{1-3}$alkyl;
$L_1$ and $L_2$ independently represent a bond or —C(=O)—;
$R^3$ represents hydrogen or $C_{1-3}$alkyl;
n represents 0, 1, 2 or 3;
$R^4$ and $R^5$ independently on each occurrence represent hydrogen, fluoro or $C_{1-3}$alkyl;
$R^6$ represents hydrogen, hydroxy, fluoro, —$NR^7R^8$, phenyl or a 5- or 6-membered heteroaryl comprising 1, 2, 3 or 4 heteroatoms individually selected from N, O and S and wherein said phenyl or heteroaryl is optionally substituted by 1, 2, 3, 4 or 5 substituents, which may be the same or different, selected from $R^9$;
$R^7$ and $R^8$ independently represent hydrogen, $C_{1-4}$alkyl or benzyl wherein the benzene ring is optionally substituted by 1, 2, 3, 4 or 5 substituents, which may be the same or different, selected from $R^9$; and
$R^9$ represents cyano, amino, halogen, hydroxy, $C_{1-4}$alkyl, $C_{2-4}$alkenyl, $C_{2-4}$alkynyl, halogen$C_{1-4}$alkyl, hydroxy$C_{1-4}$alkyl, $C_{1-4}$alkoxy, $C_{1-4}$alkylamino, di$C_{1-4}$alkylamino, $C_{1-4}$alkylcarbonyl, $C_{1-4}$alkoxycarbonyl, aminocarbonyl, aminocarbonyl$C_{1-4}$alkyl, $C_{1-4}$alkylaminocarbonyl, di$C_{1-4}$alkylaminocarbonyl or $C_{1-4}$alkoxycarbonylamino.

DEFINITIONS

As used herein, the term "$C_{1-4}$alkyl" refers to a straight or branched hydrocarbon chain radical consisting solely of carbon and hydrogen atoms, containing no unsaturation, having from one to four carbon atoms, and which is attached to the rest of the molecule by a single bond. The term "$C_{1-3}$alkyl" is to be construed accordingly. Examples of $C_{1-4}$alkyl include, but are not limited to, methyl, (R)-methyl, ethyl, n-propyl, 1-methylethyl(iso-propyl), n-butyl and 1,1-dimethylethyl(t-butyl).

As used herein, the term "$C_{2-4}$alkenyl" refers to a straight or branched hydrocarbon chain radical group consisting solely of carbon and hydrogen atoms, containing at least one double bond, having from two to four carbon atoms, which is attached to the rest of the molecule by a single bond. Examples of $C_{2-4}$alkenyl include, but are not limited to, ethenyl, prop-1-enyl and but-1-enyl.

As used herein, the term "$C_{2-4}$alkynyl" refers to a straight or branched hydrocarbon chain radical group consisting solely of carbon and hydrogen atoms, containing at least one triple bond, having from two to four carbon atoms, and which is attached to the rest of the molecule by a single bond. Examples of $C_{2-4}$alkynyl include, but are not limited to, ethynyl, prop-1-ynyl and but-1-ynyl.

As used herein, the term "$C_{1-4}$alkoxy" refers to a radical of the formula —$OR_a$ where $R_a$ is a $C_{1-4}$alkyl radical as generally defined above. Examples of $C_{1-4}$alkoxy include, but are not limited to, methoxy, ethoxy, propoxy, iso-propoxy, butoxy and isobutoxy.

As used herein, the term "$C_{1-4}$alkylcarbonyl" refers to a radical of the formula —C(=O)—$R_a$ where $R_a$ is a $C_{1-4}$alkyl radical as defined above.

As used herein, the term "$C_{1-4}$alkoxycarbonyl" refers to a radical of the formula —C(=O)—O—$R_a$ where $R_a$ is a $C_{1-4}$alkyl radical as defined above.

As used herein, the term "$C_{1-4}$alkoxycarbonylamino" refers to a radical of the formula —NH—C(=O)—O—$R_a$ where $R_a$ is a $C_{1-4}$alkyl radical as defined above.

As used herein, the term "hydroxy$C_{1-4}$alkyl" refers to a $C_{1-4}$alkyl radical as defined above, wherein one of the hydrogen atoms of the $C_{1-4}$alkyl radical is replaced by OH. Examples of hydroxy$C_{1-4}$alkyl include, but are not limited to, hydroxy-methyl, 2-hydroxy-ethyl, 2-hydroxy-propyl and 3-hydroxy-propyl and 4-hydroxy-butyl.

As used herein, the term "$C_{1-4}$alkylamino" refers to a radical of the formula —NH—$R_a$ where $R_a$ is a $C_{1-4}$alkyl radical as defined above.

As used herein, the term "di$C_{1-4}$alkylamino" refers to a radical of the formula —N($R_a$)—$R_a$ where each $R_a$ is a $C_{1-4}$alkyl radical, which may be the same or different, as defined above.

As used herein, the term "aminocarbonyl" refers to a radical of the formula —C(=O)—$NH_2$.

As used herein, the term "aminocarbonyl$C_{1-4}$alkyl" refers to a radical of the formula —$R_a$—C(=O)—$NH_2$ where $R_a$ is a $C_{1-4}$alkyl radical as defined above.

As used herein, the term "$C_{1-4}$alkylaminocarbonyl" refers to a radical of the formula —C(=O)—NH—$R_a$ where $R_a$ is a $C_{1-4}$alkyl radical as defined above.

As used herein, the term "di$C_{1-4}$alkylaminocarbonyl" refers to a radical of the formula —C(=O)—N($R_a$)—$R_a$ where each $R_a$ is a $C_{1-4}$alkyl radical, which may be the same or different, as defined above.

"Halogen" refers to bromo, chloro, fluoro or iodo.

As used herein, the term "halogen$C_{1-4}$alkyl" refers to $C_{1-4}$alkyl radical, as defined above, substituted by one or more halo radicals, as defined above. Examples of halogen$C_{1-4}$alkyl include, but are not limited to, trifluoromethyl, difluoromethyl, fluoromethyl, trichloromethyl, 2,2,2-trifluoroethyl, 1-fluoromethyl-2-fluoroethyl, 3-bromo-2-fluoropropyl and 1-bromomethyl-2-bromoethyl.

As used herein, the term "heteroaryl" refers to a 5- or 6-membered aromatic monocyclic ring radical comprising 1, 2, 3 or 4 heteroatoms individually selected from nitrogen, oxygen and sulfur. The heteroaryl radical may be bonded via a carbon atom or heteroatom. Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

As used herein, the term "a," "an," "the" and similar terms used in the context of the present invention (especially in the context of the claims) are to be construed to cover both the singular and plural unless otherwise indicated herein or clearly contradicted by the context. The use of any and all examples, or exemplary language (e.g. "such as") provided herein is intended merely to better illuminate the invention and does not pose a limitation on the scope of the invention otherwise claimed.

The term "compounds of the present invention" (unless specifically identified otherwise) refer to compounds of formula (I) or (Ia), compounds of the Examples, pharmaceutically acceptable salts of such compounds, and/or hydrates or solvates of such compounds, as well as, all stereoisomers (including diastereoisomers and enantiomers), tautomers and isotopically labeled compounds (including deuterium). The term "agents of the invention" is intended to have the same meaning as "compounds of the present invention".

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaernia, hypercoagulability and/or microalbuminemia. The American Heart Association has published guidelines for the diagnosis of metabolic syndrome, Grundy, S., et. al., (2006) Cardiol. Rev. Vol. 13, No. 6, pp. 322-327.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

As used herein, the term "prevention" of any particular disease or disorder refers to the administration of a compound of the invention to a subject before any symptoms of that disease or disorder are apparent.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, a subject is "in need of" a treatment if such subject would benefit biologically, medically or in quality of life from such treatment.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by HDAC4 or (ii) associated with HDAC4 activity, or (iii) characterized by activity (normal or abnormal) of HDAC4; or (2) reducing or inhibiting the activity of HDAC4. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of HDAC4. The meaning of the term "a therapeutically effective amount" as illustrated in the above embodiments for HDAC4 also applies by the same means to any other relevant proteins/peptides/enzymes, such as one of the other members of the histone deacetylase enzyme family.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both.

DETAILED DESCRIPTION OF THE INVENTION

The present invention provides compounds and pharmaceutical compositions thereof that may be useful in the treatment or prevention of diseases, conditions and/or disorders modulated by the inhibition of HDAC4.

Embodiment 1: a compound of formula (I), or a pharmaceutically acceptable salt thereof, as defined above.

Embodiment 2: a compound according to Embodiment 1, or a pharmaceutically acceptable salt thereof, wherein $X_1$ represents N; $X_2$ represents $CR^2$; $X_3$ represents N; and $X_4$ represents CH.

Embodiment 3: a compound according to Embodiment 2, or a pharmaceutically acceptable salt thereof, wherein $R^2$ represents hydrogen, Embodiment 4: a compound according to Embodiment 1, or a pharmaceutically acceptable salt thereof, wherein $X_1$ represents N; $X_2$ represents N; $X_3$ represents CH; and $X_4$ represents CH.

Embodiment 5: a compound according to Embodiment 1, or a pharmaceutically acceptable salt thereof, wherein $X_1$ represents $CR^1$; $X_2$ represents $CR^2$; $X_3$ represents N; and $X_4$ represents CH.

Embodiment 6: a compound according to Embodiment 5, or a pharmaceutically acceptable salt thereof, wherein $R^1$ and $R^2$ both represent hydrogen.

Embodiment 7: a compound according to Embodiment 1, or a pharmaceutically acceptable salt thereof, wherein $X_1$ represents N; $X_2$ represents $CR^2$; $X_3$ represents CH; and $X_4$ represents CH.

Embodiment 8: a compound according to Embodiment 7, or a pharmaceutically acceptable salt thereof, wherein $R^2$ represents hydrogen or chloro.

Embodiment 9: a compound according to Embodiment 7, or a pharmaceutically acceptable salt thereof, wherein $R^2$ represents chloro.

Embodiment 10: a compound according to Embodiment 1, or a pharmaceutically acceptable salt thereof, wherein $X_1$ represents $CR^1$; $X_2$ represents $CR^2$; $X_3$ represents N; and $X_4$ represents N.

Embodiment 11: a compound according to Embodiment 10, or a pharmaceutically acceptable salt thereof, wherein $R^1$ and $R^2$ both represent hydrogen.

Embodiment 12: a compound according to Embodiment 1, or a pharmaceutically acceptable salt thereof, wherein $X_1$ represents $CR^1$, $X_2$ represents N; $X_3$ represents N; and $X_4$ represents CH.

Embodiment 13: a compound according to Embodiment 12, or a pharmaceutically acceptable salt thereof, wherein $R^1$ represents hydrogen.

Embodiment 14: a compound according to any one of Embodiments 1 to 13, or a pharmaceutically acceptable salt thereof, wherein $L_1$ represents a bond.

Embodiment 15: a compound according to any one of Embodiments 1 to 13, or a pharmaceutically acceptable salt thereof, wherein $L_1$ represents —C(=O)—.

Embodiment 16: a compound according to any one of Embodiments 1 to 15, or a pharmaceutically acceptable salt thereof, wherein $R^3$ represents hydrogen.

Embodiment 17: a compound according to any one of Embodiments 1 to 15, or a pharmaceutically acceptable salt thereof, wherein $R^3$ represents methyl.

Embodiment 18: a compound according to any one of Embodiments 1 to 17, or a pharmaceutically acceptable salt thereof, wherein $L_2$ represents a bond.

Embodiment 19: a compound according to any one of Embodiments 1 to 17, or a pharmaceutically acceptable salt thereof, wherein $L_2$ represents —C(=O)—.

Embodiment 20: a compound according to any one of Embodiments 1 to 19, or a pharmaceutically acceptable salt thereof, wherein n represents 1.

Embodiment 21: a compound according to any one of Embodiments 1 to 19, or a pharmaceutically acceptable salt thereof, wherein n represents 2.

Embodiment 22: a compound according to any one of Embodiments 1 to 21, or a pharmaceutically acceptable salt thereof, wherein $R^4$ and $R^5$ independently on each occurrence represent hydrogen or $C_{1-3}$alkyl.

Embodiment 23: a compound according to any one of Embodiments 1 to 19, or a pharmaceutically acceptable salt thereof, wherein n represents 0.

Embodiment 24: a compound according to any one of Embodiments 1 to 23, or a pharmaceutically acceptable salt thereof, wherein $R^6$ represents —$NR^7R^8$.

Embodiment 25: a compound according to any one of Embodiments 1 to 23, or a pharmaceutically acceptable salt thereof, wherein $R^6$ represents phenyl or a 6-membered heteroaryl comprising 1, 2, 3 or 4 heteroatoms individually selected from N, O and S and wherein said phenyl or heteroaryl is optionally substituted by 1, 2 or 3 substituents, which may be the same or different, selected from $R^9$.

Embodiment 26: a compound according to any one of Embodiments 1 to 23, or a pharmaceutically acceptable salt thereof, wherein $R^6$ represents phenyl, pyridine-2-yl, pyridine-3-yl or pyridine-4-yl and wherein said phenyl or pyridine is optionally substituted by 1, 2 or 3 substituents, which may be the same or different, selected from $R^9$.

Embodiment 27: a compound according to any one of Embodiments 1 to 23, or a pharmaceutically acceptable salt thereof, wherein $R^6$ represents phenyl, pyridine-2-yl, pyridine-3-yl or pyridine-4-yl and wherein said phenyl or pyridine is optionally substituted by a single substituent selected from $R^9$.

Embodiment 28: a compound according to any one of Embodiments 1 to 24, or a pharmaceutically acceptable salt thereof, wherein $R^7$ and $R^8$ independently represent hydrogen, methyl, ethyl or benzyl.

Embodiment 29: a compound according to any one of Embodiments 1 to 27, or a pharmaceutically acceptable salt thereof, wherein $R^9$ represents cyano, amino, halogen, hydroxy or $C_{1-3}$alkyl.

Embodiment 30: a compound according to any one of Embodiments 1 to 27, or a pharmaceutically acceptable salt thereof, wherein $R^9$ represents cyano, amino or methyl.

Embodiment 31: a compound according to any one of Embodiments 1 to 23, or a pharmaceutically acceptable salt thereof, wherein $R^6$ represents hydrogen, hydroxy or fluoro.

Embodiment 32: a compound according to Embodiment 1 of formula (Ia), or a pharmaceutically acceptable salt thereof,

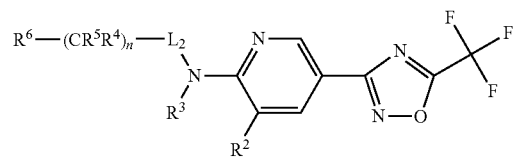

(Ia)

wherein
$R^2$ represents hydrogen, chloro or $C_{1-3}$alkyl;
$R^3$ represents hydrogen or $C_{1-3}$alkyl;
$L_2$ represents a bond or —C(=O)—;
n represents 0, 1, 2 or 3;
$R^4$ and $R^5$ independently on each occurrence represent hydrogen, fluoro or $C_{1-3}$alkyl;
$R^6$ represents hydrogen, hydroxy, fluoro, —$NR^7R^8$, phenyl or a 5- or 6-membered heteroaryl comprising 1, 2, 3 or 4 heteroatoms individually selected from N, O and S and wherein said phenyl or heteroaryl is optionally substituted by 1, 2, 3, 4 or 5 substituents, which may be the same or different, selected from $R^9$;
$R^7$ and $R^8$ independently represent hydrogen, $C_{1-4}$alkyl or benzyl wherein the benzene ring is optionally substituted by 1, 2, 3, 4 or 5 substituents, which may be the same or different, selected from $R^9$; and
$R^9$ represents cyano, amino, halogen, hydroxy, $C_{1-4}$alkyl, $C_{2-4}$alkenyl, $C_{2-4}$alkynyl, halogen$C_{1-4}$alkyl, hydroxy$C_{1-4}$alkyl, $C_{1-4}$alkoxy, $C_{1-4}$alkylamino, di$C_{1-4}$alkylamino, $C_{1-4}$alkylcarbonyl, $C_{1-4}$alkoxycarbonyl, aminocarbonyl, aminocarbonyl$C_{1-4}$alkyl, $C_{1-4}$alkylaminocarbonyl, di$C_{1-4}$alkylaminocarbonyl or $C_{1-4}$alkoxycarbonylamino.

Embodiment 33: a compound according to Embodiment 1 of formula (Ia), or a pharmaceutically acceptable salt thereof,
wherein
$R^2$ represents hydrogen or chloro;
$R^3$ represents hydrogen or $C_{1-3}$alkyl;
$L_2$ represents a bond;
n represents 0, 1, 2 or 3;
$R^4$ and $R^5$ independently on each occurrence represent hydrogen, fluoro or $C_{1-3}$alkyl;
$R^6$ represents phenyl or a 6-membered heteroaryl comprising 1, 2, 3 or 4 heteroatoms individually selected from N, O and S and wherein said phenyl or heteroaryl is optionally substituted by 1, 2 or 3 substituents, which may be the same or different, selected from $R^9$; and
$R^9$ represents cyano, amino, halogen, hydroxy, $C_{1-4}$alkyl, $C_{2-4}$alkenyl, $C_{2-4}$alkynyl, halogen$C_{1-4}$alkyl, hydroxy$C_{1-4}$alkyl, $C_{1-4}$alkoxy, $C_{1-4}$alkylamino, di$C_{1-4}$alkylamino, $C_{1-4}$alkylcarbonyl, $C_{1-4}$alkoxycarbonyl, aminocarbonyl, aminocarbonyl$C_{1-4}$alkyl, $C_{1-4}$alkylaminocarbonyl, di$C_{1-4}$alkylaminocarbonyl or $C_{1-4}$alkoxycarbonylamino.

Embodiment 34: a compound according to Embodiment 1 of formula (Ia), or a pharmaceutically acceptable salt thereof,
wherein
$R^2$ represents hydrogen or chloro;
$R^3$ represents hydrogen or $C_{1-3}$alkyl;
$L_2$ represents a bond;
n represents 1 or 2;
$R^4$ and $R^5$ independently on each occurrence represent hydrogen, fluoro or $C_{1-3}$alkyl;
$R^6$ represents phenyl, pyridine-2-yl, pyridine-3-yl or pyridine-4-yl and wherein said phenyl or pyridine is optionally substituted by 1, 2 or 3 substituents, which may be the same or different, selected from R$^9$; and R$^9$ represents cyano, amino, halogen, hydroxy or C$_{1-3}$alkyl.

Embodiment 35: a compound according to Embodiment 1, which is selected from:

N-(5-(5-(trifluoromethyl)-1,2,4-oxadiazol-3-yl)pyrazin-2-yl)acetamide;
4-Cyano-N-(5-(5-(trifluoromethyl)-1,2,4-oxadiazol-3-yl)pyrazin-2-yl)benzamide;
N-methyl-N-(pyridin-4-ylmethyl)-5-(5-(trifluoromethyl)-1,2,4-oxadiazol-3-yl)pyrimidin-2-amine;
N-benzyl-5-(5-(trifluoromethyl)-1,2,4-oxadiazol-3-yl)pyrimidin-2-amine;
N-((2-chloropyridin-4-yl)methyl)-N-methyl-5-(5-(trifluoromethyl)-1,2,4-oxadiazol-3-yl)pyrimidin-2-amine;
N-(pyridin-4-ylmethyl)-5-(5-(trifluoromethyl)-1,2,4-oxadiazol-3-yl)pyrimidin-2-amine;
N-(1-phenylethyl)-5-(5-(trifluoromethyl)-1,2,4-oxadiazol-3-yl)pyrimidin-2-amine;
N-((6-methylpyridin-3-yl)methyl)-5-(5-(trifluoromethyl)-1,2,4-oxadiazol-3-yl)pyrimidin-2-amine;
N-(1-(pyridin-4-yl)ethyl)-5-(5-(trifluoromethyl)-1,2,4-oxadiazol-3-yl)pyrimidin-2-amine;
N-(pyridin-3-ylmethyl)-5-(5-(trifluoromethyl)-1,2,4-oxadiazol-3-yl)pyrimidin-2-amine;
N-((6-methylpyridin-2-yl)methyl)-5-(5-(trifluoromethyl)-1,2,4-oxadiazol-3-yl)pyrimidin-2-amine;
N-(1-phenylethyl)-5-(5-(trifluoromethyl)-1,2,4-oxadiazol-3-yl)pyrimidin-2-amine;
N-(1-phenylpropyl)-5-(5-(trifluoromethyl)-1,2,4-oxadiazol-3-yl)pyrimidin-2-amine;
N-methyl-N-(2-(pyridin-4-yl)ethyl)-5-(5-(trifluoromethyl)-1,2,4-oxadiazol-3-yl)pyrimidin-2-amine;
N-(1-(pyridin-4-yl)propyl)-5-(5-(trifluoromethyl)-1,2,4-oxadiazol-3-yl)pyrimidin-2-amine;
N-(1-(2-methylpyridin-4-yl)ethyl)-5-(5-(trifluoromethyl)-1,2,4-oxadiazol-3-yl)pyrimidin-2-amine;
N-methyl-N-((2-methylpyridin-4-yl)methyl)-5-(5-(trifluoromethyl)-1,2,4-oxadiazol-3-yl)pyrimidin-2-amine;
N-(1-(dimethylamino)propan-2-yl)-6-(5-(trifluoromethyl)-1,2,4-oxadiazol-3-yl)nicotinamide;
N-(1-hydroxypropan-2-yl)-6-(5-(trifluoromethyl)-1,2,4-oxadiazol-3-yl)nicotinamide;
N-(1-(benzyl(methyl)amino)propan-2-yl)-6-(5-(trifluoromethyl)-1,2,4-oxadiazol-3-yl)nicotinamide;
N-(1-(diethylamino)-3-methylbutan-2-yl)-6-(5-(trifluoromethyl)-1,2,4-oxadiazol-3-yl)nicotinamide;
N-(1-(diethylamino)propan-2-yl)-6-(5-(trifluoromethyl)-1,2,4-oxadiazol-3-yl)nicotinamide;
N-(1-(dimethylamino)propan-2-yl)-5-(5-(trifluoromethyl)-1,2,4-oxadiazol-3-yl)picolinamide;
3-chloro-N-(1-(dimethylamino)propan-2-yl)-5-(5-(trifluoromethyl)-1,2,4-oxadiazol-3-yl)picolinamide;
N-(1-(dimethylamino)propan-2-yl)-2-(5-(trifluoromethyl)-1,2,4-oxadiazol-3-yl)pyrimidine-5-carboxamide;
N-benzyl-6-(5-(trifluoromethyl)-1,2,4-oxadiazol-3-yl)pyridin-3-amine;
N-benzyl-5-(5-(trifluoromethyl)-1,2,4-oxadiazol-3-yl)pyridin-2-amine;
N-(1-phenylethyl)-5-(5-(trifluoromethyl)-1,2,4-oxadiazol-3-yl)pyridin-2-amine;
N-(pyridin-3-ylmethyl)-5-(5-(trifluoromethyl)-1,2,4-oxadiazol-3-yl)pyridin-2-amine;
N-(pyridin-4-ylmethyl)-5-(5-(trifluoromethyl)-1,2,4-oxadiazol-3-yl)pyridin-2-amine;
N-((6-methylpyridin-3-yl)methyl)-5-(5-(trifluoromethyl)-1,2,4-oxadiazol-3-yl)pyridin-2-amine;
N-benzyl-3-chloro-5-(5-(trifluoromethyl)-1,2,4-oxadiazol-3-yl)pyridin-2-amine;
3-chloro-N-(1-phenylethyl)-5-(5-(trifluoromethyl)-1,2,4-oxadiazol-3-yl)pyridin-2-amine;
3-chloro-N-(pyridin-4-ylmethyl)-5-(5-(trifluoromethyl)-1,2,4-oxadiazol-3-yl)pyridin-2-amine;
3-chloro-N-(1-(pyridin-4-yl)ethyl)-5-(5-(trifluoromethyl)-1,2,4-oxadiazol-3-yl)pyridin-2-amine;
3-chloro-N-(pyridin-3-ylmethyl)-5-(5-(trifluoromethyl)-1,2,4-oxadiazol-3-yl)pyridin-2-amine;
3-Chloro-N-((6-methylpyridin-3-yl)methyl)-5-(5-(trifluoromethyl)-1,2,4-oxadiazol-3-yl)pyridin-2-amine;
3-chloro-N-(pyridin-2-ylmethyl)-5-(5-(trifluoromethyl)-1,2,4-oxadiazol-3-yl)pyridin-2-amine;
N-benzyl-6-(5-(trifluoromethyl)-1,2,4-oxadiazol-3-yl)pyridazin-3-amine;
N-(1-Phenylethyl)-2-(5-(trifluoromethyl)-1,2,4-oxadiazol-3-yl)pyrimidin-5-amine;
N-(Pyridin-4-ylmethyl)-2-(5-(trifluoromethyl)-1,2,4-oxadiazol-3-yl)pyrimidin-5-amine;
N-(Pyridin-4-yl)ethyl)-5-(5-trifluoromethyl-1,2,4-oxadiazol-3-yl)pyridin-2-amine;
N-(1-(Pyridin-4-yl)ethyl)-6-(5-(trifluoromethyl)-1,2,4-oxadiazol-3-yl)pyridazin-3-amine;
N-(1-(benzyl(methyl)amino)propan-2-yl)-6-(5-(trifluoromethyl)-1,2,4-oxadiazol-3-yl)nicotinamide;
and pharmaceutically acceptable salts thereof.

Embodiment 36: a compound according to Embodiment 1, which is selected from:

N-(5-(5-(trifluoromethyl)-1,2,4-oxadiazol-3-yl)pyrazin-2-yl)acetamide;
4-Cyano-N-(5-(5-(trifluoromethyl)-1,2,4-oxadiazol-3-yl)pyrazin-2-yl)benzamide;
N-methyl-N-(pyridin-4-ylmethyl)-5-(5-(trifluoromethyl)-1,2,4-oxadiazol-3-yl)pyrimidin-2-amine;
N-benzyl-5-(5-(trifluoromethyl)-1,2,4-oxadiazol-3-yl)pyrimidin-2-amine;
N-((2-chloropyridin-4-yl)methyl)-N-methyl-5-(5-(trifluoromethyl)-1,2,4-oxadiazol-3-yl)pyrimidin-2-amine;
N-(pyridin-4-ylmethyl)-5-(5-(trifluoromethyl)-1,2,4-oxadiazol-3-yl)pyrimidin-2-amine;
N-(1-phenylethyl)-5-(5-(trifluoromethyl)-1,2,4-oxadiazol-3-yl)pyrimidin-2-amine;
N-((6-methylpyridin-3-yl)methyl)-5-(5-(trifluoromethyl)-1,2,4-oxadiazol-3-yl)pyrimidin-2-amine;
N-(1-(pyridin-4-yl)ethyl)-5-(5-(trifluoromethyl)-1,2,4-oxadiazol-3-yl)pyrimidin-2-amine;
N-(pyridin-3-ylmethyl)-5-(5-(trifluoromethyl)-1,2,4-oxadiazol-3-yl)pyrimidin-2-amine;
N-((6-methylpyridin-2-yl)methyl)-5-(5-(trifluoromethyl)-1,2,4-oxadiazol-3-yl)pyrimidin-2-amine;
(R)—N-(1-phenylethyl)-5-(5-(trifluoromethyl)-1,2,4-oxadiazol-3-yl)pyrimidin-2-amine;
(R)—N-(1-phenylpropyl)-5-(5-(trifluoromethyl)-1,2,4-oxadiazol-3-yl)pyrimidin-2-amine;
N-methyl-N-(2-(pyridin-4-yl)ethyl)-5-(5-(trifluoromethyl)-1,2,4-oxadiazol-3-yl)pyrimidin-2-amine;
N-(1-(pyridin-4-yl)propyl)-5-(5-(trifluoromethyl)-1,2,4-oxadiazol-3-yl)pyrimidin-2-amine;
N-(1-(2-methylpyridin-4-yl)ethyl)-5-(5-(trifluoromethyl)-1,2,4-oxadiazol-3-yl)pyrimidin-2-amine;
N-methyl-N-((2-methylpyridin-4-yl)methyl)-5-(5-(trifluoromethyl)-1,2,4-oxadiazol-3-yl)pyrimidin-2-amine;
(R)—N-(1-(dimethylamino)propan-2-yl)-6-(5-(trifluoromethyl)-1,2,4-oxadiazol-3-yl)nicotinamide;
N-(1-(dimethylamino)propan-2-yl)-6-(5-(trifluoromethyl)-1,2,4-oxadiazol-3-yl)nicotinamide;

(S)—N-(1-hydroxypropan-2-yl)-6-(5-(trifluoromethyl)-1,2,4-oxadiazol-3-yl)nicotinamide;
(R)—N-(1-(benzyl(methyl)amino)propan-2-yl)-6-(5-(trifluoromethyl)-1,2,4-oxadiazol-3-yl)nicotinamide;
(R)—N-(1-(diethylamino)-3-methylbutan-2-yl)-6-(5-(trifluoromethyl)-1,2,4-oxadiazol-3-yl)nicotinamide;
(R)—N-(1-(diethylamino)propan-2-yl)-6-(5-(trifluoromethyl)-1,2,4-oxadiazol-3-yl)nicotinamide;
(R)—N-(1-(dimethylamino)propan-2-yl)-5-(5-(trifluoromethyl)-1,2,4-oxadiazol-3-yl)picolinamide;
(R)-3-chloro-N-(1-(dimethylamino)propan-2-yl)-5-(5-(trifluoromethyl)-1,2,4-oxadiazol-3-yl)picolinamide;
(R)—N-(1-(dimethylamino)propan-2-yl)-2-(5-(trifluoromethyl)-1,2,4-oxadiazol-3-yl)pyrimidine-5-carboxamide;
N-benzyl-6-(5-(trifluoromethyl)-1,2,4-oxadiazol-3-yl)pyridin-3-amine;
N-benzyl-5-(5-(trifluoromethyl)-1,2,4-oxadiazol-3-yl)pyridin-2-amine;
N-(1-phenylethyl)-5-(5-(trifluoromethyl)-1,2,4-oxadiazol-3-yl)pyridin-2-amine;
N-(pyridin-3-ylmethyl)-5-(5-(trifluoromethyl)-1,2,4-oxadiazol-3-yl)pyridin-2-amine;
N-(pyridin-4-ylmethyl)-5-(5-(trifluoromethyl)-1,2,4-oxadiazol-3-yl)pyridin-2-amine;
N-((6-methylpyridin-3-yl)methyl)-5-(5-(trifluoromethyl)-1,2,4-oxadiazol-3-yl)pyridin-2-amine;
N-benzyl-3-chloro-5-(5-(trifluoromethyl)-1,2,4-oxadiazol-3-yl)pyridin-2-amine;
(R)-3-chloro-N-(1-phenylethyl)-5-(5-(trifluoromethyl)-1,2,4-oxadiazol-3-yl)pyridin-2-amine;
3-chloro-N-(pyridin-4-ylmethyl)-5-(5-(trifluoromethyl)-1,2,4-oxadiazol-3-yl)pyridin-2-amine;
3-chloro-N-(1-(pyridin-4-yl)ethyl)-5-(5-(trifluoromethyl)-1,2,4-oxadiazol-3-yl)pyridin-2-amine;
3-chloro-N-(pyridin-3-ylmethyl)-5-(5-(trifluoromethyl)-1,2,4-oxadiazol-3-yl)pyridin-2-amine;
3-Chloro-N-((6-methylpyridin-3-yl)methyl)-5-(5-(trifluoromethyl)-1,2,4-oxadiazol-3-yl)pyridin-2-amine;
3-chloro-N-(pyridin-2-ylmethyl)-5-(5-(trifluoromethyl)-1,2,4-oxadiazol-3-yl)pyridin-2-amine;
N-benzyl-6-(5-(trifluoromethyl)-1,2,4-oxadiazol-3-yl)pyridazin-3-amine;
(R)—N-(1-Phenylethyl)-2-(5-(trifluoromethyl)-1,2,4-oxadiazol-3-yl)pyrimidin-5-amine;
(S)—N-(1-Phenylethyl)-2-(5-(trifluoromethyl)-1,2,4-oxadiazol-3-yl)pyrimidin-5-amine;
N-(Pyridin-4-ylmethyl)-2-(5-(trifluoromethyl)-1,2,4-oxadiazol-3-yl)pyrimidin-5-amine;
(R)—N-(Pyridin-4-yl)ethyl)-5-(5-trifluoromethyl-1,2,4-oxadiazol-3-yl)pyridin-2-amine;
(R)—N-(1-(Pyridin-4-yl)ethyl)-6-(5-(trifluoromethyl)-1,2,4-oxadiazol-3-yl)pyridazin-3-amine;
(R)—N-(1-(benzyl(methyl)amino)propan-2-yl)-6-(5-(trifluoromethyl)-1,2,4-oxadiazol-3-yl)nicotinamide;
and pharmaceutically acceptable salts thereof.

On account of one or more than one asymmetrical carbon atom, which may be present in a compound of the formula (I), a corresponding compound of the formula (I) may exist in pure optically active form or in the form of a mixture of optical isomers, e. g. in the form of a racemic mixture. All of such pure optical isomers and all of their mixtures, including the racemic mixtures, are part of the present invention.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. Where a compound comprising one or more chiral centers is drawn herein with the stereochemistry indicated in the drawn structure, then the individual optical isomer is intended. Where a compound comprising one or more chiral centers is drawn herein without the stereochemistry indicated in the drawn structure, then no one specific optical isomer is intended and the drawn chemical structure may represent any optical isomer or mixture of isomers having that structure, for example a racemic or diastereomeric mixture.

In one embodiment, there is provided a compound of the Examples as an isolated stereoisomer wherein the compound has one stereocenter and the stereoisomer is in the R configuration.

In one embodiment, there is provided a compound of the Examples as an isolated stereoisomer wherein the compound has one stereocenter and the stereoisomer is in the S configuration.

In one embodiment, there is provided a compound of the Examples, wherein the compound has one stereocenter, as a racemic mixture.

It is also possible that the intermediates and compounds of the present invention may exist in different tautomeric forms, and all such forms are embraced within the scope of the invention. The term "tautomer" or "tautomeric form"

refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the terms "salt" or "salts" refers to an acid addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. The compounds of the present invention may be capable of forming acid salts by virtue of the presence of amino groups or groups similar thereto.

In one embodiment, the invention relates to a compound of the formula (I) or (Ia) as defined herein, in free form. In another embodiment, the invention relates to a compound of the formula (I) or (Ia) as defined herein, in salt form. In another embodiment, the invention relates to a compound of the formula (I) or (Ia) as defined herein, in acid addition salt form. In a further embodiment, the invention relates to a compound of the formula (I) or (Ia) as defined herein, in pharmaceutically acceptable salt form. In yet a further embodiment, the invention relates to a compound of the formula (I) or (Ia) as defined herein, in pharmaceutically acceptable acid addition salt form. In yet a further embodiment, the invention relates to any one of the compounds of the Examples in free form. In yet a further embodiment, the invention relates to any one of the compounds of the Examples in salt form. In yet a further embodiment, the invention relates to any one of the compounds of the Examples in acid addition salt form. In yet a further embodiment, the invention relates to any one of the compounds of the Examples in pharmaceutically acceptable salt form. In still another embodiment, the invention relates to any one of the compounds of the Examples in pharmaceutically acceptable acid addition salt form.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

The pharmaceutically acceptable salts of the present invention can be synthesized from an acidic moiety, by conventional chemical methods. Generally, such salts can be prepared by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds of the present invention, including their salts, may also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

The compounds of the present invention, including salts, hydrates and solvates thereof, may inherently or by design form polymorphs.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation); at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the present invention may be synthesized by synthetic routes that include processes analogous to those well-known in the chemical arts, particularly in light of the description contained herein. The starting materials are generally available from commercial sources such as Sigma-Aldrich or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesise the compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In a further aspect, the invention relates to a process for the preparation of a compound of the formula (I), in free form or in pharmaceutically acceptable salt form, comprising
(a) when $L_1$ is a bond $L_2$, —C(=O)— and $R^3$ is hydrogen, the reaction of a compound of the formula (II)

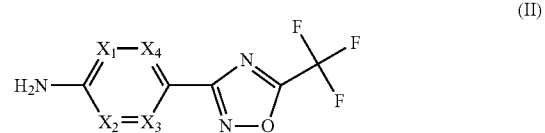

wherein $X_1$, $X_2$, $X_3$, and $X_4$ are as defined for formula (I), with a compound of formula (III),

wherein n, $R^4$, $R^5$ and $R^6$ are as defined for formula (I);
(b) when $L_1$ is a bond, $L_2$ is a bond and $R^3$ is hydrogen, the reaction of a compound of the formula (II)

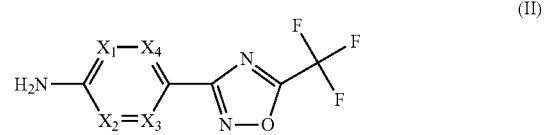

wherein $X_1$, $X_2$, $X_3$, and $X_4$ are as defined for formula (I), with a compound of formula (III),

wherein n, $R^4$, $R^5$ and $R^6$ are as defined for formula (I);
(c) when $L_1$ is a bond, $L_2$ is a bond and $R^3$ is hydrogen, the reaction of a compound of the formula (V)

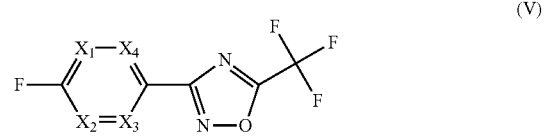

wherein $X_1$, $X_2$, $X_3$, and $X_4$ are as defined for formula (I), with a compound of formula (VI),

wherein n, $R^4$, $R^5$ and $R^6$ are as defined for formula (I);

(d) when $L_1$ is —C(=O)— and $R^3$ is hydrogen, the reaction of a compound of the formula (VII)

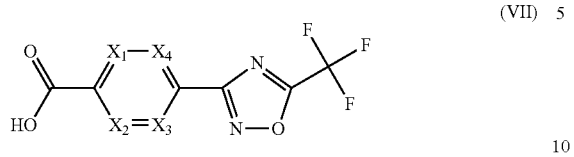
(VII)

wherein $X_1$, $X_2$, $X_3$ and $X_4$ are as defined for formula (I), with a compound of formula (VIII)

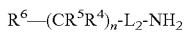
(VIII)

wherein $L_2$, n, $R^4$, $R^5$ and $R^6$ are as defined for formula (I); or (e) the reaction of a compound of the formula (IX)

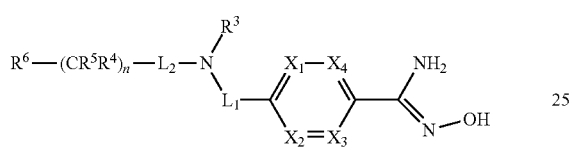
(IX)

wherein $X_1$, $X_2$, $X_3$, $X_4$, $L_1$, $L_2$, $R^3$, $R^4$, $R^5$ and $R^6$ are as defined for formula (I), with trifluoroacetic acid anhydride; and thereafter i) the optional reduction, oxidation or other functionalisation of the resulting compound,
ii) the cleavage of any protecting group present,
iii) the recovery of the so obtainable compound of the formula (I) in free form or in pharmaceutically acceptable salt form, and
iv) the optional separation of mixtures of optically active isomers into their individual optically active isomeric forms.

The above reactions can be effected according to conventional methods. For example, the reaction described in step (a) may be carried out in the presence of a suitable solvent, for example pyridine, and at a suitable temperature, for example 10 to 50° C., more suitably 18 to 30° C.

The reaction described in step (b) may be carried out in the presence of a suitable solvent, for example DMF, optionally in the presence of a suitable base, for example cesium carbonate, and at a suitable temperature, for example 50 to 150° C., more suitably 100 to 150° C.

The reaction described in step (c) may be carried out in the presence of a suitable solvent, for example n-butanol, optionally in the presence of a suitable base, for example DIPEA, and at a suitable temperature, for example 50 to 150° C., more suitably 80 to 120° C.

The reaction described in step (d) may be carried out using a suitable coupling agent, for example HATU O-(7-Azabenzotriazol-1-yl)-N,N,N',N'-tetramethyluronium hexafluorophosphate, a suitable solvent, for example DMF, a suitable base, for example DIPEA, and at a suitable temperature, for example 10 to 50° C., more suitably 18 to 30° C.

The reaction described in step (e) may be carried out in the presence of a suitable solvent, for example THF, and at a suitable temperature, for example 0 to 25° C., more suitably 2 to 10° C.

Compounds of formula (XII) wherein $X_1$, $X_2$, $X_3$, and $X_4$ are as defined for formula (I) and Y represents amino, fluoro or carboxy may be prepared according to Scheme 1 below from compounds of formula (X) which are described in the literature, are commercially available or can be made using methods known to those skilled in the art.

Scheme 1: general procedure for the synthesis of compounds of formula (XII):

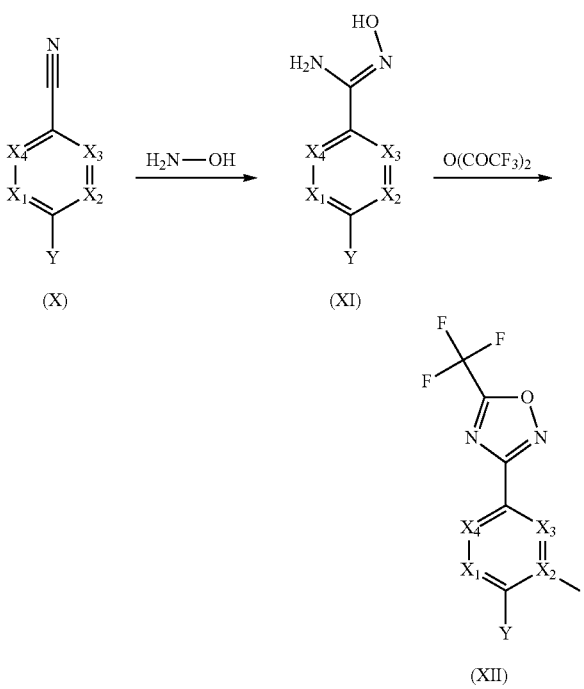

Compounds of formula (IX) may be prepared according to Scheme 2 below from compounds of formula (XIII) which are described in the literature, are commercially available or can be made using methods known to those skilled in the art and as described herein.

Scheme 2: general procedure for the synthesis of compounds of formula (IX):

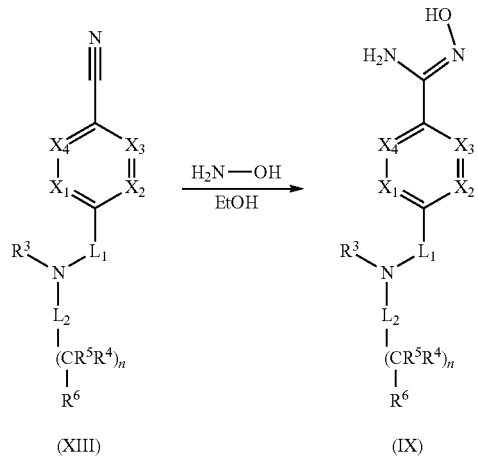

The compounds of formulae (III), (IV), (VI), (VIII), (X) and (XIII) are known or may be prepared according to conventional procedures starting from known compounds, may be prepared from known compounds as described in the Examples or may be prepared using procedures analogous to those described in the Examples.

The further optional reduction, oxidation or other functionalisation of compounds of formula (I) may be carried out according to methods well know to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, and in H.-D. Jakubke and H. Jeschkeit, "Aminosäuren, Peptide, Proteine" (Amino acids, Peptides, Proteins), Verlag Chemie, Weinheim, Deerfield Beach, and Basel 1982. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, acid addition salts of compounds of the present invention are obtained in customary manner, e.g. by treating the compounds with an acid or a suitable anion exchange reagent.

Salts can be converted into the free compounds in accordance with methods known to those skilled in the art and as described in the Examples. Acid addition salts can be converted, for example, by treatment with a suitable basic agent.

For those compounds containing an asymmetric carbon atom, the compounds exist in individual optically active isomeric forms or as mixtures thereof, e.g. as racemic or diastereomeric mixtures. Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Enantiomers can also be separated by use of a commercially available chiral HPLC column.

The invention further includes any variant of the present processes, in which the reaction components are used in the form of their salts or optically pure material. Compounds of the invention and intermediates can also be converted into each other according to methods generally known to those skilled in the art.

Compounds of the formula (I), in free form or in pharmaceutically acceptable salt form, hereinafter often referred to as "agents of the invention", exhibit valuable pharmacological properties, when tested in vitro, and may, therefore, be useful in medicaments, in therapy or for use as research chemicals, for example as tool compounds.

Biological Assays

The agents of the invention are inhibitors of HDAC4. The inhibiting properties of a compound of the invention towards HDAC4 versus HDAC1 and HDAC6 can be evaluated in the assays described below.

Test 1: HDAC4 Assay Description

Human recombinant HDAC4 was expressed in full length form (aa 2-1084) in Sf9 insect cells (obtained from ATCC) using baculovirus generated with Bac-to-Bac system (Invitrogen). Test compounds were serially diluted to reach final test concentrations from 0.000128 µM to 10 µM. HDAC4 and test compounds were incubated in 25 mM Tris buffer pH 8.0 containing 137 mM NaCl, 2.7 mM KCl, 1 mM $MgCl_2$, 0.05% (w/v) bovine serum albumine and 0.005% (v/v) Triton-X-100 for 2 hours at room temperature in presence of 5 µM of acetyl-Gly-Ala-Lys(ε-trifluoroacetyl)-AMC (AMC=7-amino-4-methyl coumarin) in a final volume of 9 µl. Control wells with HDAC4 only (positive control) and without HDAC4 (negative control) were included on the microplate. Bovine trypsin (4.5 µl of a 300 nM solution) was added and the plate incubated for additional 15 minutes at room temperature. The plate was placed in a fluorescence microplate reader, and read at an excitation wavelength of 360 nm and an emission wavelength of 450 nm with a 10 nm bandpath. Fluorescence values for all wells containing HDAC4 (positive control and wells with test compound) were corrected by subtracting negative control fluorescence values, and $IC_{50}$ values were calculated by fitting the dose-response curves to a 4-parameter logistic function.

Test 2: HDAC1 Assay Description

A similar assay procedure as described in Test 1 was used for HDAC1. Human recombinant full length HDAC1 expressed in a baculovirus expression system was purchased from BPS BioSciences (San Diego, Calif., U.S.A.). The substrate used in the HDAC1 assay was 5 µM of acetyl-Gly-Ala-Lys(acetyl)-AMC.

Test 3: HDAC6 Assay Description

A similar assay procedure as described in Test 1 was used for HDAC6. Human recombinant full length HDAC6 expressed in a baculovirus expression system was purchased from BPS BioSciences (San Diego, Calif., U.S.A.). The substrate used in the HDAC1 assay was 5 µM of acetyl-Gly-Ala-Lys (acetyl)-AMC.

The compounds of the Examples showed the $IC_{50}$ values presented in Table 1 below when tested in the HDAC assays.

TABLE 1

| Example Number | HDAC1 $IC_{50}$ (µM) | HDAC4 $IC_{50}$ (µM) | HDAC6 $IC_{50}$ (µM) | Example Number | HDAC1 $IC_{50}$ (µM) | HDAC4 $IC_{50}$ (µM) | HDAC6 $IC_{50}$ (µM) |
|---|---|---|---|---|---|---|---|
| 1 | >10 | 0.46 | 1.7 | 2 | >10 | 1.4 | 2.6 |
| 3 | 3.2 | 0.039 | 6.7 | 4 | >10 | 0.036 | 0.32 |
| 5 | 1.7 | 0.04 | 2.1 | 6 | 0.62 | 0.044 | 0.99 |
| 7 | >10 | 0.12 | >0.4 | 8 | 3 | 0.025 | 0.25 |

TABLE 1-continued

| Example Number | HDAC1 IC$_{50}$ (μM) | HDAC4 IC$_{50}$ (μM) | HDAC6 IC$_{50}$ (μM) | Example Number | HDAC1 IC$_{50}$ (μM) | HDAC4 IC$_{50}$ (μM) | HDAC6 IC$_{50}$ (μM) |
|---|---|---|---|---|---|---|---|
| 9 | 4.1 | 0.022 | 0.56 | 10 | 6.6 | 0.14 | 1.1 |
| 11 | 0.51 | 0.24 | 0.55 | 12 | 3.5 | 0.049 | 0.34 |
| 13 | 1.7 | 0.022 | 0.14 | 14 | 7.6 | 0.11 | >10 |
| 15 | 2.6 | 0.02 | 0.21 | 16 | 1.6 | 0.044 | 0.35 |
| 17 | 2.2 | 0.034 | 3.5 | 18 | >10 | 0.25 | >10 |
| 19 | 1.7 | 0.35 | >10 | 20 | >10 | 4.3 | >10 |
| 21 | >10 | 0.018 | >10 | 22 | >10 | 0.16 | >10 |
| 23 | >10 | 0.028 | >10 | 24 | >10 | 0.99 | >10 |
| 25 | >10 | 3.6 | >10 | 26 | >10 | 0.42 | >10 |
| 27 | 9.6 | 2.8 | >10 | 28 | >10 | 0.073 | 3 |
| 29 | 6.2 | 0.027 | 0.64 | 30 | 6.1 | 0.079 | 1.8 |
| 31 | 4.5 | 0.041 | 1.6 | 32 | 2.4 | 0.063 | 0.77 |
| 33 | >10 | 0.093 | >10 | 34 | 6.3 | 0.047 | 4.5 |
| 35 | 1.1 | 0.011 | 1.8 | 36 | 0.86 | 0.0064 | 1.1 |
| 37 | 1.2 | 0.019 | 2 | 38 | 1.4 | 0.021 | 1.55 |
| 39 | 2.5 | 0.037 | 1.9 | 40 | 7.9 | 0.2 | 0.84 |
| 41 | 4 | 0.06 | 1.3 | 42 | >10 | 5 | 1.9 |
| 43 | 4.7 | 0.19 | 1.1 | 44 | 2.7 | 0.029 | 1.03 |
| 45 | 3.2 | 0.065 | 0.61 | 46 | >10 | 0.066 | >10 |

Note that N-(pyridin-4-ylmethyl)-2-(5-(trifluoromethyl)-1,2,4-oxadiazol-3-yl)pyrimidine-5-carboxamide and (R)—N-(1-phenylethyl)-2-(5-(trifluoromethyl)-1,2,4-oxadiazol-3-yl)pyrimidine-5-carboxamide were tested in an earlier version of the HDAC4 assay (described below) and found to have an IC$_{50}$ value greater than 30 μM.

Description of Earlier Version of HDAC4 Assay

Human recombinant HDAC4 was expressed in full length form (aa 2-1084) in Sf9 insect cells (obtained from ATCC) using baculovirus generated with Bac-to-Bac system (Invitrogen). Test compounds were serially diluted to reach final test concentrations from 0.003 μM to 100 μM. HDAC4 and test compounds were incubated in 25 mM Tris buffer pH 8.0 containing 137 mM NaCl, 2.7 mM KCl, 1 mM MgCl$_2$ and 0.05% (w/v) bovine serum albumine for 2 hours at room temperature in presence of 10 μM of acetyl-Gly-Ala-Lys(ε-trifluoroacetyl)-AMC (AMC=7-amino-4-methyl coumarin) in a final volume of 200 μl. Control wells with HDAC4 only (positive control) and without HDAC4 (negative control) were included on the microplate. Bovine trypsin (10 μl of a 0.4 mg/ml solution) was added and the plate incubated for additional 15 minutes at room temperature. The plate was placed in a fluorescence microplate reader, and read at an excitation wavelength of 360 nm and an emission wavelength of 450 nm with a cut-off filter of 435 nm. Fluorescence values for all wells containing HDAC4 (positive control and wells with test compound) were corrected by subtracting negative control fluorescence values, and IC$_{50}$ values were calculated by fitting the dose-response curves to a 4-parameter logistic function.

Due to their ability to inhibit HDAC4 activity, agents of the invention may be useful in the treatment or prevention neurodegeneration arising from cerebral ischemia; an acute, traumatic or chronic degenerative process of the nervous system, such as Parkinson's disease, Down's syndrome, dementia, e.g. senile dementia, dementia with Lewy bodies or a fronto-temporal dementia, a cognitive disorder, cognitive impairment, e.g. mild cognitive impairment, memory impairment, an amyloid neuropathy, a peripheral neuropathy, Alzheimer's disease, Gerstmann-Straeussler-Scheinker syndrome, Niemann-Pick disease, e.g. Niemann-Pick type C disease, brain inflammation, a brain, spinal cord or nerve injury, e.g. traumatic brain injury (TBI), a nerve trauma or a brain trauma, vascular amyloidosis, cerebral haemorrhage with amyloidosis, Huntington's chorea, amyotrophic lateral sclerosis, multiple sclerosis or fragile×syndrome; scrapie; cerebral amyloid angiopathy; an encephalopathy, e.g. transmissible spongiform encephalopathy; or stroke. Agents of the invention may also be useful in enhancing cognition, e.g. in a subject suffering from a dementing condition, such as Alzheimer's disease; or as ligands, e.g. radioligands or positron emission tomography (PET) ligands.

Due to their ability to inhibit HDAC4 activity, agents of the invention may also be useful in the treatment or prevention metabolic syndrome (including but not limited to dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia, bulimia and anorexia), weight loss, wasting disorders, body mass index and leptin-related diseases.

Due to their ability to inhibit HDAC4 activity, agents of the invention may also be useful in the treatment or prevention of muscular atrophy, such as that found as a result of: the catabolic side effects of glucocorticoids; chronic fatigue syndrome; chronic myalgia; bone fracture; acute fatigue syndrome; immobilization due to bed rest, as when a patient undergoes elective surgery or an extended hospital stay due to disease; cachexia; chronic catabolic state; eating disorders; side effects of chemotherapy; wasting secondary to fractures; wasting in connection with chronic obstructive pulmonary disease (COPD), chronic liver disease, AIDS, weightlessness, cancer cachexia, burn and trauma recovery, chronic catabolic state such as coma, eating disorders such as anorexia and chemotherapy; wasting in connection with renal failure; wasting as a result of liver failure; low testosterone or low IGF1 or low growth hormone levels. The therapy may also be useful in settings of lipodistrophy; obesity; sarcopenia—which is defined as age-related frailty or age-related loss of muscle; reduced muscle strength and function. The therapy may also be helpful in settings of myositis leading to muscle loss, such as Inclusion Body Myositis, or any of the inflammatory myosites.

For the above-mentioned indications, the appropriate dosage will vary depending on, e. g., the compound employed as active pharmaceutical ingredient, the host, the mode of administration, the nature and severity of the condition, disease or disorder or the effect desired. However, in general, satisfactory results in animals are indicated to be obtained at a daily dosage of from about 0.1 to about 100, preferably from about 1 to about 50, mg/kg of animal body weight. In larger mammals, for example humans, an indicated daily dosage is in the range of from about 0.5 to about 2000, preferably from about 2 to about 200, mg of an agent of the invention conveniently administered, for example, in divided doses up to four times a day or in sustained release form.

An agent of the invention may be administered by any conventional route, in particular enterally, preferably orally, e. g. in the form of a tablet or capsule, or parenterally, e. g. in the form of an injectable solution or suspension.

In a further aspect, the invention relates to a pharmaceutical composition comprising an agent of the invention as active pharmaceutical ingredient in association with at least one pharmaceutically acceptable carrier or diluent and optionally in association with other auxiliary substances, such as inhibitors of cytochrome P450 enzymes, agents preventing the degradation of active pharmaceutical ingredients by cytochrome P450, agents improving or enhancing the pharmacokinetics of active pharmaceutical ingredients, agents improving or enhancing the bioavailability of active pharmaceutical ingredients, and so on, e. g. grapefruit juice, ketoconazole or, preferably, ritonavir. Such a composition may be manufactured in conventional manner, e. g. by mixing its components. Unit dosage forms contain, e. g., from about 0.1 to about 1000, preferably from about 1 to about 500, mg of an agent of the invention.

In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

In accordance with the foregoing, in a further aspect, the invention relates to an agent of the invention for use as a medicament, for example for the treatment or prevention of neurodegeneration, muscle atrophy or metabolic syndrome. In a further embodiment, the invention relates to an agent of the invention for use in the treatment of a disease or disorder mediated by HDAC4 activity. In one embodiment, the invention relates to an agent of the invention for use in the treatment of Huntington's disease, muscle atrophy or diabetes/metabolic syndrome. In another embodiment, the invention relates to an agent of the invention for use in the treatment of muscle atrophy.

In a further aspect, the invention relates to the use of an agent of the invention as an active pharmaceutical ingredient in a medicament, for example for the treatment or prevention of neurodegeneration, muscle atrophy or metabolic syndrome. In a further embodiment, the invention relates to the use of an agent of the invention as an active pharmaceutical ingredient in a medicament for the treatment or prevention of a disease or disorder mediated by HDAC4 activity. In one embodiment, the invention relates to the use of an agent of the invention as an active pharmaceutical ingredient in a medicament for the treatment or prevention of Huntington's disease, muscle atrophy or diabetes/metabolic syndrome.

In a further aspect, the invention relates to the use of an agent of the invention for the manufacture of a medicament for the treatment or prevention of neurodegeneration, muscle atrophy or metabolic syndrome. In a further embodiment, the invention relates to the use of an agent of the invention for the manufacture of a medicament for the treatment or prevention of a disease or disorder mediated by HDAC4 activity. In one embodiment, the invention relates to the use of an agent of the invention for the manufacture of a medicament for the treatment or prevention of Huntington's disease, muscle atrophy or diabetes/metabolic syndrome.

In a further aspect, the invention relates to a method for the treatment or prevention of neurodegeneration, muscle atrophy or metabolic syndrome, in a subject in need of such treatment or prevention, which method comprises administering to such subject an effective amount of an agent of the invention. In one embodiment, the invention relates to a method of modulating HDAC4 activity in a subject, wherein the method comprises administering to the subject a therapeutically effective amount of an agent of the invention. In another embodiment, the invention relates to a method for the treatment or prevention of a disease mediated by HDAC4 activity, in a subject in need of such treatment or prevention, which method comprises administering to such subject an effective amount of an agent of the invention. In yet another embodiment, the invention relates to a method for the treatment or prevention of Huntington's disease, muscle atrophy or diabetes/metabolic syndrome, in a subject in need of such treatment or prevention, which method comprises administering to such subject an effective amount of an agent of the invention.

An agent of the invention can be administered as sole active pharmaceutical ingredient or as a combination with at least one other active pharmaceutical ingredient effective, e. g., in the treatment or prevention of neurodegeneration, muscle atrophy or metabolic syndrome. Such a pharmaceutical combination may be in the form of a unit dosage form, which unit dosage form comprises a predetermined quantity of each of the at least two active components in association with at least one pharmaceutically acceptable carrier or diluent. Alternatively, the pharmaceutical combination may be in the form of a package comprising the at least two active components separately, e. g. a pack or dispenser-device adapted for the concomitant or separate administration of the at least two active components, in which these active components are separately arranged. In a further aspect, the invention relates to such pharmaceutical combinations.

In a further aspect, the invention therefore relates to a pharmaceutical combination comprising a therapeutically effective amount of an agent of the invention and a second drug substance, for simultaneous or sequential administration.

In one embodiment, the invention provides a product comprising an agent of the invention and at least one other therapeutic agent as a combined preparation for simultaneous, separate or sequential use in therapy. In one embodiment, the therapy is the treatment of a disease or condition mediated by HDAC4 activity.

In one embodiment, the invention provides a pharmaceutical composition comprising an agent of the invention and another therapeutic agent(s). Optionally, the pharmaceutical composition may comprise a pharmaceutically acceptable carrier or diluent, as described above.

In one embodiment, the invention provides a kit comprising two or more separate pharmaceutical compositions, at least one of which contains an agent of the invention. In one embodiment, the kit comprises means for separately retaining said compositions, such as a container, divided bottle, or divided foil packet. An example of such a kit is a blister pack, as typically used for the packaging of tablets, capsules and the like. The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the agent of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent. Accordingly, the invention provides an agent of the invention for use in the treatment of a disease or condition mediated by HDAC4 activity, wherein the medicament is prepared for administration with another therapeutic agent. The invention also provides the use of another therapeutic agent for treating a disease or condition mediated by HDAC4 activity, wherein the medicament is administered with an agent of the invention.

The invention also provides an agent of the invention for use in a method of treating a disease or condition mediated HDAC4 activity, wherein the agent of the invention is prepared for administration with another therapeutic agent. The invention also provides another therapeutic agent for use in a method of treating a disease or condition mediated by HDAC4 activity, wherein the other therapeutic agent is prepared for administration with an agent of the invention. The invention also provides an agent of the invention for use in a method of treating a disease or condition mediated by HDAC4 activity, wherein the agent of the invention is administered with another therapeutic agent. The invention also provides another therapeutic agent for use in a method of treating a disease or condition mediated by HDAC4 activity, wherein the other therapeutic agent is administered with an agent of the invention.

The invention also provides the use of an agent of the invention for treating a disease or condition mediated by HDAC4 activity, wherein the patient has previously (e.g. within 24 hours) been treated with another therapeutic agent. The invention also provides the use of another therapeutic agent for treating a disease or condition mediated by HDAC4 activity, wherein the patient has previously (e.g. within 24 hours) been treated with an agent of the invention.

In one embodiment, the invention relates to a compound of the invention in combination with another therapeutic agent wherein the other therapeutic agent is selected from:
(a) acetylcholinesterase inhibitors, such as donepezil (Aricept™), rivastigmine (Exelon™) and galantamine (Razadyne™);
(b) glutamate antagonists, such as memantine (Namenda™);
(c) antidepressant medications for low mood and irritability, such as citalopram (Celexa™), fluoxetine (Prozac™), paroxeine (Paxil™), sertraline (Zoloft™) and trazodone (Desyrel™);
(d) anxiolytics for anxiety, restlessness, verbally disruptive behavior and resistance, such as lorazepam (Ativan™) and oxazepam (Serax™);
(e) antipsychotic medications for hallucinations, delusions, aggression, agitation, hostility and uncooperativeness, such as aripiprazole (Abilify™), clozapine (Clozaril™), haloperidol (Haldol™), olanzapine (Zyprexa™), quetiapine (Seroquel™), risperidone (Risperdal™) and ziprasidone (Geodon™);
(f) mood stabilizers, such as carbamazepine (Tegretol™) and divalproex (Depakote™);
(g) nicotinic alpha—7 agonists;
(h) mGluR5 antagonists;
(i) H3 agonists; and
(j) amyloid therapy vaccines.

Thus, in another embodiment, the invention provides a pharmaceutical composition comprising:
i) a compound of the invention, or a pharmaceutically acceptable salt thereof; and
ii) at least one compound selected from:
  (a) acetylcholinesterase inhibitors,
  (b) glutamate antagonists,
  (c) antidepressant medications,
  (d) anxiolytics,
  (e) antipsychotic medications,
  (f) mood stabilizers,
  (g) nicotinic alpha—7 agonists,
  (h) mGluR5 antagonists,
  (i) H3 agonists; and
ii) one or more pharmaceutically acceptable excipient, diluent or carrier.

In another embodiment, the invention relates to a compound of the invention, or a pharmaceutically acceptable salt thereof, in combination with another therapeutic agent wherein the other therapeutic agent is selected from:
a) antidiabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as vildagliptin;
b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid×receptor) and LXR (liver×receptor) ligands; cholestyramine; fibrates; nicotinic acid bile acid binding resins such as cholestyramine; fibrates; nicotinic acid and other GPR109 agonists; cholesterol absorption inhibitors such as ezetimibe; CETP inhibitors (cholesterol-ester-transfer-protein inhibitors), and aspirin;
c) anti-obesity agents such as orlistat, sibutramine and Cannabinoid Receptor 1 (CB1) antagonists e.g. rimonabant; and
d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.
e) agonists of peroxisome proliferator-activator receptors, such as fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethylphenyl)-oxazol-4-ylmethoxy]-benzenesulfonyl}-2,3-dihydro-1H-indole-2-carboxylic or a salt thereof.

Thus, in one embodiment, the invention provides a pharmaceutical composition comprising:
i) a compound of the invention, or a pharmaceutically acceptable salt thereof; and
ii) at least one compound selected from:
   a) antidiabetic agents,
   b) hypolipidemic agents,
   c) anti-obesity agents,
   d) anti-hypertensive agents,
   e) agonists of peroxisome proliferator-activator receptors; and
ii) one or more pharmaceutically acceptable carrier or diluent.

Other specific anti-diabetic compounds are described by Patel Mona in *Expert Opin Investig Drugs,* 2003, 12(4), 623-633, in the FIGS. 1 to 7.

In another embodiment, the invention relates to a compound of the invention, or a pharmaceutically acceptable salt thereof, in combination with another therapeutic agent wherein the other therapeutic agent is selected from:
a) inhibitors of the myostatin receptor(s),
b) activators of the IGF1 receptor,
c) activators of the beta2 adrenergic receptor,
d) inhibitors of TNF, and
e) activators of the androgen receptor.

Thus, in one embodiment, the invention provides a pharmaceutical composition comprising:
i) a compound of the invention, or a pharmaceutically acceptable salt thereof; and
ii) at least one compound selected from:
   a) inhibitors of the myostatin receptor(s);
   b) activators of the IGF1 receptor;
   c) activators of the beta2 adrenergic receptor;
   d) inhibitors of TNF; and
   e) activators of the androgen receptor; and
ii) one or more pharmaceutically acceptable carrier or diluent.

The structure of the therapeutic agents identified by code numbers, generic or trade names may be taken from the actual edition of the standard compendium "The Merck Index" or from databases, e.g., Patents International (e.g. IMS World Publications).

EXAMPLES

NMR Methods

Proton spectra were recorded on Varian Mercury 400 MHz or Bruker Avance 400 or 600 MHz instruments. Chemical shifts are reported in ppm relative to methanol ($\delta$ 3.31), dimethyl sulfoxide ($\delta$ 2.50), or chloroform ($\delta$ 7.26).

Chromatography and LC/MS Methods for Examples 1 to 17

Flash Chromatography System

ISCO System, CombiFlash Companion; IG Instrumenten-Gesellschaft AG. Cartusch System.
UPLC-MS System (Analytical): Waters
Column: Waters Acquity HSST3 1.8 µm 2.1×50 mm at 50° C.
Eluent: (A) Water+0.05% formic acid+3.75 mM ammonium acetate;
(B) Acetonitrile+0.04% formic acid; from 2 to 98% B in 1.4 min
Flow rate: 1.2 mL/min; temp. 37° C.
Method A
LaChrom Elite, Hitachi, HPLC system
Column: VWR Chromolith SpeedRod RP-18e, 3.5 µm, 4.6×50 mm;
Eluent: Water (+0.1% formic acid): acetonitrile (0.08% formic acid) from 95:5 to 5:95 in 3.5 min, hold 95% B for 1.0 min, re-equilibrate for 1.5 min;
Flow rate: 1.5 ml/min; temp. 37° C.

Chromatography and LC/MS Methods for Examples 18 to 46

Flash Chromatography System:
Isolera Four, Biotage
Preparative HPLC Chromatography:
Gilson GX281
Column: Sunfire C18, 5 µm, 30×100 mm;
Eluent: A: water (+0.1% TFA)
   B: acetonitrile
Gradient: 95:5 to 0:100 in 20 min
Flow rate: 30 mL/min
Temperature: 24° C.
LC-MS System (Analytical):
Method B
Agilent 1100 HPLC Series including MS with chemical ionisation
Column: Symmetry C8, 3.5 µm, 2×50 mm;
Eluent: A: water (+0.1% TFA)
   B: acetonitrile (+0.1% TFA)
Gradient: 90:10 to 5:95 in 2 min
Flow rate: 1.0 mL/min
Temperature: 50° C.
Method C
Waters Acquity UPLC including MS with electrospray ionisation (ESI)
Column: Waters Aquity HSS T3, 1.8 µm, 2.1×50 mm;
Eluent: A: water (+0.05% formic acid+3-75 mM ammonium acetate)
   B: acetonitrile (+0.04% formic acid)
Gradient: 98:2 to 2:98 in 1.40 min
Flow rate: 1.2 mL/min
Temperature: 50° C.
Method D
Waters 2795 Alliance HT HPLC instrument with electrospray ionisation
Column: SunFire C18, 3.5 µm, 4.6×20 mm;
Eluent: A: water (+0.1% TFA)
   B: acetonitrile (+0.1% TFA)
Gradient: 95:05 to 0:100 in 4.0 min
Flow rate: 3.0 mL/min
Temperature: 45° C.

Abbreviations aa amino acid
APCI atmospheric pressure chemical ionisation
BINAP 2,2'-bis(diphenylphosphino)-1,1'-binaphthyl
BOC tert-butoxycarbonyl
ca circa (approximately)
conc. concentrated
d day(s)
DIPEA N,N-diisopropylethylamine
DMF dimethylformamide
DMSO dimethylsulfoxide EDC 1-(3-dimethylaminopropyl)-3-ethylcarbodiimide
ESIMS electrospray ionisation mass spectrometry
EtOH ethanol
$Et_2O$ diethyl ether
h hour(s)
HATU O-(7-Azabenzotriazol-1-yl)-N,N,N',N'-tetramethyluronium hexafluorophsphate
HOBT 1-Hydroxybenzotriazole trihydrate
HPLC high pressure liquid chromatography
HV high vacuum (<0.01 mbar)
$IC_{50}$ half maximal inhibitory concentration
i.V. in vacuo
LCMS liquid chromatography mass spectroscopy
min minute(s)
MS mass spectroscopy
NMR nuclear magnetic resonance spectrometry
RT retention time
rt room temperature
THF tetrahydrofuran
TFA trifluoroacetic acid
UPLC ultra performance liquid chromatography Example 1

N-(5-(5-(trifluoromethyl)-1,2,4-oxadiazol-3-yl)pyrazin-2-yl)acetamide

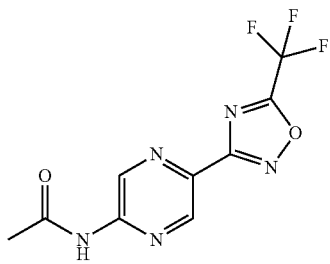 [SMILES: CC(=O)Nc1cnc(-c2noc(C(F)(F)F)n2)cn1]

5-Amino-N'-hydroxypyrazine-2-carboximidamide

To 2-amino-5-cyanopyrazine (Ark Pharm Inc) (4.87 g, 40.5 mmol) and hydroxylamine hydrochloride (6.20 g, 89 mmol) in EtOH (30 mL) was added triethylamine (9.44 g, 93 mmol). The reaction was stirred at 80° C. for 1 h. The precipitate was filtered, washed with a small volume ethanol and dried on high vacuum to give 6-amino-N'-hydroxypyrazine-2-carboximidamide (5.9 g, 38.5 mmol, 95% yield) as a yellow powder. HPLC RT=0.593 min (Method A), ESIMS $[M+H]^+=154$ 5-(5-(trifluoromethyl)-1,2,4-oxadiazol-3-yl)pyrazin-2-amine To 5-amino-N'-hydroxypyrazine-2-carboximidamide (1.12 g, 7.31 mmol) in dry THF (6 mL) at rt was added 2,2,2-trifluoroacetic anhydride (4.61 g, 21.94 mmol). The dark-yellow solution was then heated up and stirred at reflux temperature for 16 h. Subsequently the reaction was quenched by addition of a 25 mol % ammonia solution to reach a basic pH. Brine was added and the product extracted with ethyl acetate. The combined organic layers were dried over sodium sulfate, filtered and the organic solvent evaporated under reduced pressure. The resulting crude residue (3.75 g) was dissolved in methanol (20 mL) and the resulting yellow solution heated to reflux temperature for 6 h. Subsequently the solvent was evaporated, the remaining residue dried at high vacuum. The crude product was dissolved in ethyl acetate, washed with saturated sodium carbonate solution and brine. The organic layer was dried over sodium sulfate, filtered and the solvent evaporated to give Klaeust9-001-EXP081 5-(5-(trifluoromethyl)-1,2,4-oxadiazol-3-yl)pyrazin-2-amine (1.84 g, 7.56 mmol, 66% yield) as brown solid. HPLC RT=2.910 min (Method A), ESIMS $[M+H]^+=232$ N-(5-(5-(trifluoromethyl)-1,2,4-oxadiazol-3-yl)pyrazin-2-yl)acetamide To 5-(5-(trifluoromethyl)-1,2,4-oxadiazol-3-yl)pyrazin-2-amine (60 mg, 0.26 mmol) in pyridine (2.5 mL) the acetyl chloride (22.4 mg, 0.286 mmol) was added. The reaction was stirred for 2 h at rt. Subsequently the reaction solvent was evaporated under reduced pressure and the crude residue was subjected to flash chromatography (ISCO CombiFlash Rf; 24 g silicagel, dichlormethane/methanol) to give N-(5-(5-(trifluoromethyl)-1,2,4-oxadiazol-3-yl)pyrazin-2-yl)acetamide (20 mg, 0.07 mmol, 28% yield) as yellow powder. HPLC RT=3.053 min (Method A), ESIMS $[M+H]^+=274$, 1H NMR (400 MHz, DMSO-$d_6$) δ ppm 11.2 (s, 1H), 9.52 (d, J=1.38 Hz, 1H) 9.09 (d, J=1.51 Hz, 1H) 2.20 (s, 3H)

Example 2

4-Cyano-N-(5-(5-(trifluoromethyl)-1,2,4-oxadiazol-3-yl)pyrazin-2-yl)benzamide

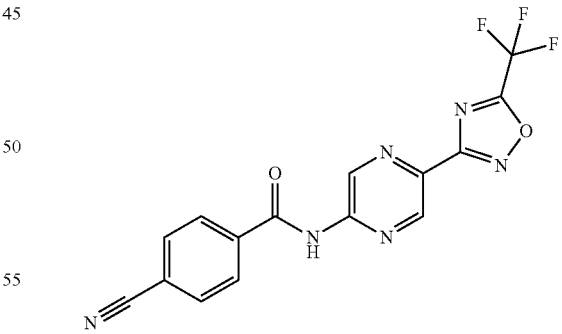

4-Cyano-N-(5-(5-(trifluoromethyl)-1,2,4-oxadiazol-3-yl)pyrazin-2-yl)benzamide was made using a process analogous to that described in Example 1 HPLC RT=3.577 min (Method A), ESIMS $[M+H]^+=361$, light pink powder 1H NMR (400 MHz, DMSO-$d_6$) δ ppm 11.92-11.95 (m, 1H) 9.64-9.66 (m, 1H) 9.19-9.22 (m, 1H) 8.21-8.24 (m, 1H) 8.19-8.22 (m, 1H) 8.07-8.09 (m, 1H) 8.05-8.07 (m, 1H)

Example 3

N-methyl-N-(pyridin-4-ylmethyl)-5-(5-(trifluoromethyl)-1,2,4-oxadiazol-3-yl)pyrimidin-2-amine

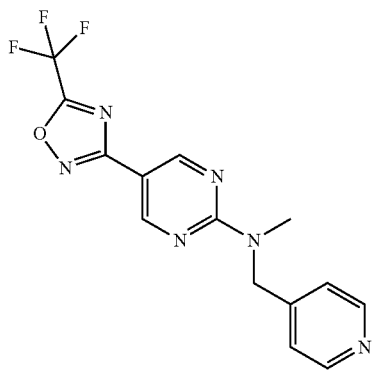 [SMILES: CN(Cc1ccncc1)c1ncc(-c2noc(C(F)(F)F)n2)cn1]

2-(methyl(pyridin-4-ylmethyl)amino)pyrimidine-5-carbonitrile

To a solution of 2-(methylthio)pyrimidine-5-carbonitrile (Biofine International Inc.) (390 mg, 2.58 mmol) in 1,4-dioxane (3 mL), N-methyl-1-(pyridin-4-yl)methanamine (Fisher Scientific International—Maybridge) (789 mg, 2.50 mmol) was added at rt. The resulting reaction mixture was heated in the microwave oven at 170° C. for 10 h. Subsequently the solvent was evaporated at high vacuum and the remaining oily residue subjected to purification by flash chromatography (ISCO CombiFlash Rf; 80 g silicagel, dichlormethane/methanol) to give 2-(methyl(pyridin-4-ylmethyl)amino)pyrimidine-5-carbonitrile (404 mg, 1.65 mmol, 64% yield) as yellow powder. HPLC RT 1.323 min (Method A); ESIMS [M+1]$^+$ 226

N'-hydroxy-2-(methyl(pyridin-4-ylmethyl)amino)pyrimidine-5-carboximidamide

To a mixture of 2-(methyl(pyridin-4-ylmethyl)amino)pyrimidine-5-carbonitrile (400 mg, 01.78 mmol) in ethanol (6 mL), hydroxylamine hydrochloride (271 mg, 3.91 mmol) and triethylamine (413 mg, 4.08 mmol) were added. The yellow reaction mixture was heated to 80° C. and stirred for 1 h. Subsequently the reaction mixture was cooled to 5° C. and stirred. The precipitating white product was filtered off and dried at high vacuum to give N'-hydroxy-2-(methyl(pyridin-4-ylmethyl)amino)pyrimidine-5-carboximidamide (304 mg, 1.12 mmol, 63% yield) as white powder. HPLC RT 0.570 min (Method A); ESIMS [M+1]$^+$ 259

N-methyl-N-(pyridin-4-ylmethyl)-5-(5-(trifluoromethyl)-1,2,4-oxadiazol-3-yl)pyrimidin-2-amine A mixture of N'-hydroxy-2-(methyl(pyridin-4-ylmethyl)amino)pyrimidine-5-carboximidamide (300 mg, 1.162 mmol) in THF (4 mL) was cooled to 5° C. and 2,2,2-trifluoroacetic anhydride (732 mg, 3.480 mmol) was added drop-wise then the reaction temperature was stirred at 5° C. for 15 min. Subsequently the reaction mixture was concentrated at high vacuum and the crude product was subjected to flash chromatography (ISCO CombiFlash Rf; 40 g silicagel, dichlormethane/methanol). Fractions containing the product were combined and evaporated at reduced pressure and the residue was dried on high vacuum to give N-methyl-N-(pyridin-4-ylmethyl)-5-(5-(trifluoromethyl)-1,2,4-oxadiazol-3-yl)pyrimidin-2-amine (302 mg, 0.889 mmol, 77% yield) as white powder; Rt=2.817 min (Method A), ESIMS [M+H]$^+$=337; $^1$H NMR (400 MHz, METHANOL-d$_4$) d ppm 8.89-9.16 (m, 2H) 8.69-8.77 (m, 2H) 7.83-7.90 (m, 2H) 5.22-5.28 (m, 2H) 3.43 (s, 3H); 1H NMR (400 MHz, DMSO-d6) δ ppm 9.05-9.08 (m, 1H) 8.91-8.93 (m, 1H) 8.71 (d, J=6.27 Hz, 2H) 7.62 (d, J=5.90 Hz, 2H) 5.13 (s, 2H) 3.31 (s, 3H)

The following Examples 4 to 17 were prepared using a process analogous to that described for Example 3.

Example 4

N-benzyl-5-(5-(trifluoromethyl)-1,2,4-oxadiazol-3-yl)pyrimidin-2-amine (TFA-salt)

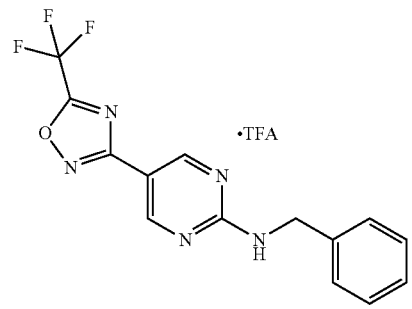 [SMILES: FC(F)(F)c1nc(-c2cnc(NCc3ccccc3)nc2)no1]

HPLC RT 3.973 min (Method A) ESIMS [M+1]$^+$ 322, white residue

1H NMR (400 MHz, DMSO-d$_6$) δ ppm 8.89 (s, 1H) 8.89 (s, 1H) 8.69-8.71 (m, 1H) 7.30-7.35 (m, 4H) 7.21-7.28 (m, 1H) 4.59-4.64 (m, 2H)

Example 5

N-((2-chloropyridin-4-yl)methyl)-N-methyl-5-(5-(trifluoromethyl)-1,2,4-oxadiazol-3-yl)pyrimidin-2-amine (TFA-salt)

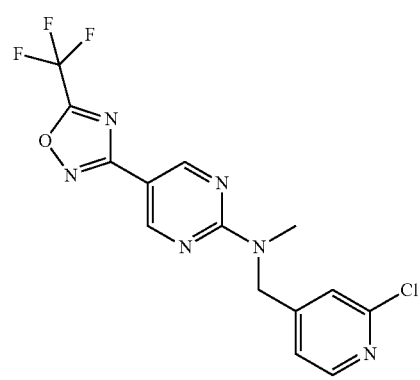 [SMILES: CN(Cc1ccnc(Cl)c1)c1ncc(-c2noc(C(F)(F)F)n2)cn1]

HPLC RT 3.977 min (Method A) ESIMS [M+1]$^+$ 371, white residue

1H NMR (400 MHz, DMSO-d$_6$) δ ppm 8.88-9.10 (m, 2H) 8.36 (d, J=5.14 Hz, 1H) 7.38 (s, 1H) 7.27 (dd, J=5.14, 1.38 Hz, 1H) 5.01 (s, 2H) 3.28 (s, 3H)

Example 6

N-(pyridin-4-ylmethyl)-5-(5-(trifluoromethyl)-1,2,4-oxadiazol-3-yl)pyrimidin-2-amine

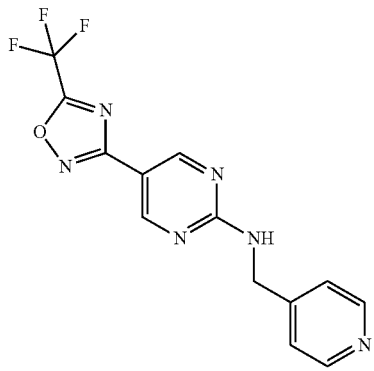 [SMILES: FC(F)(F)c1nc(-c2cnc(NCc3ccncc3)nc2)no1]

HPLC RT 2.590 min (Method A) ESIMS [M+1]$^+$ 323, white residue

1H NMR (400 MHz, DMSO-d$_6$) δ ppm 8.96-8.99 (s, 1H) 8.85-8.87 (s, 2H) 8.77 (d, J=6.40 Hz, 2H) 7.82 (d, J=6.40 Hz, 2H) 4.83 (d, J=6.15 Hz, 2H)

Example 7

N-(1-phenylethyl)-5-(5-(trifluoromethyl)-1,2,4-oxadiazol-3-yl)pyrimidin-2-amine

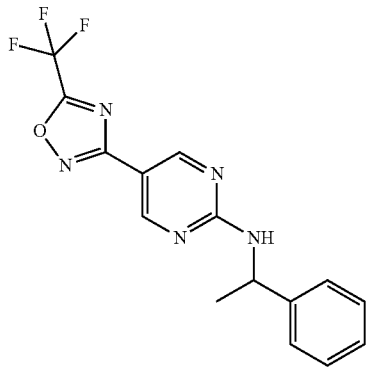 [SMILES: CC(Nc1ncc(-c2noc(C(F)(F)F)n2)cn1)c1ccccc1]

HPLC RT 4.090 min (Method A) ESIMS [M+1]$^+$ 336, white residue

1H NMR (400 MHz, DMSO-d$_6$) δ ppm 8.81-8.92 (m, 2H) 8.69-8.76 (m, 1H) 7.28-7.44 (m, 4H) 7.18-7.26 (m, 1H) 5.23 (s, 1H) 1.45-1.53 (m, 3H)

Example 8

N-((6-methylpyridin-3-yl)methyl)-5-(5-(trifluoromethyl)-1,2,4-oxadiazol-3-yl)pyrimidin-2-amine

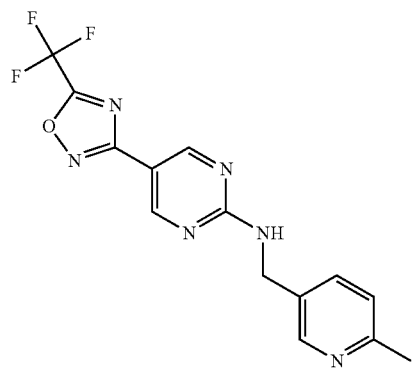 [SMILES: Cc1ccc(CNc2ncc(-c3noc(C(F)(F)F)n3)cn2)cn1]

HPLC RT 2.623 min (Method A) ESIMS [M+1]$^+$ 337, yellow residue

1H NMR (400 MHz, DMSO-d$_6$) δ ppm 8.86-8.97 (m, 2H) 8.69-8.78 (m, 1H) 8.56-8.64 (s, 1H) 7.96-8.09 (m, 1H) 7.51-7.59 (m, 1H) 4.62-4.71 (m, 2H) 2.55-2.57 (s, 3H)

Example 9

N-(1-(pyridin-4-yl)ethyl)-5-(5-(trifluoromethyl)-1,2,4-oxadiazol-3-yl)pyrimidin-2-amine

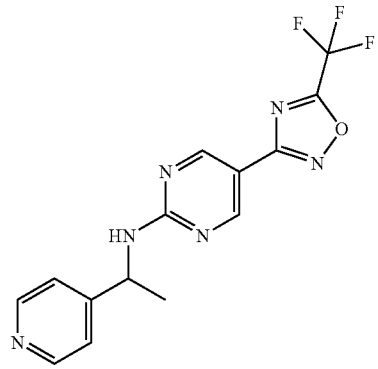 [SMILES: CC(Nc1ncc(-c2noc(C(F)(F)F)n2)cn1)c1ccncc1]

HPLC RT 2.663 min (Method A) ESIMS [M+1]$^+$ 337, white residue

1H NMR (400 MHz, DMSO-d$_6$) δ ppm 8.94 (br. s., 1H) 8.88 (d, J=7.40 Hz, 1H) 8.82 (br. s., 1H) 8.68 (d, J=5.27 Hz, 2H) 7.71 (d, J=5.14 Hz, 2H) 5.22-5.35 (m, 1H) 1.53 (d, J=7.03 Hz, 3H)

Example 10

N-(pyridin-3-ylmethyl)-5-(5-(trifluoromethyl)-1,2,4-oxadiazol-3-yl)pyrimidin-2-amine

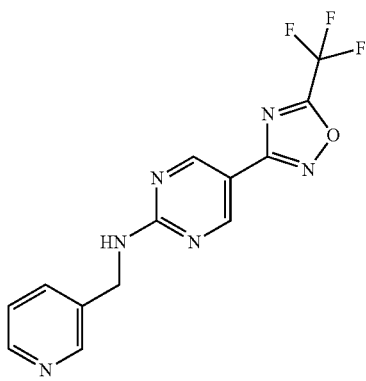 [SMILES: FC(F)(F)c1nc(-c2cnc(NCc3cccnc3)nc2)no1]

HPLC RT 2.640 min (Method A) ESIMS [M+1]$^+$ 323, white residue

1H NMR (400 MHz, DMSO-d$_6$) δ ppm 8.92 (d, J=4.02 Hz, 2H) 8.72-8.78 (m, 1H) 8.69 (d, J=1.38 Hz, 1H) 8.56-8.62 (m, 1H) 7.98-8.05 (m, 1H) 7.56-7.64 (m, 1H) 4.69 (d, J=6.15 Hz, 2H)

Example 11

N-((6-methylpyridin-2-yl)methyl)-5-(5-(trifluoromethyl)-1,2,4-oxadiazol-3-yl)pyrimidin-2-amine

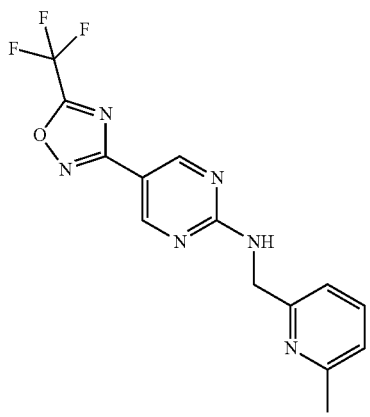 [SMILES: Cc1cccc(CNc2ncc(-c3noc(C(F)(F)F)n3)cn2)n1]

HPLC RT 2.693 min (Method A) ESIMS [M+1]$^+$ 337, white-yellow residue

1H NMR (400 MHz, DMSO-d$_6$) δ ppm 8.85-8.99 (m, 2H) 8.68-8.78 (m, 1H) 7.79-7.92 (m, 1H) 7.22-7.41 (m, 2H) 4.72 (d, J=5.90 Hz, 2H) 2.55 (s, 3H)

Example 12

(R)—N-(1-phenylethyl)-5-(5-(trifluoromethyl)-1,2,4-oxadiazol-3-yl)pyrimidin-2-amine

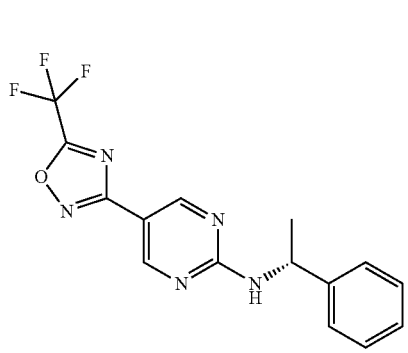 [SMILES: C[C@@H](Nc1ncc(-c2noc(C(F)(F)F)n2)cn1)c1ccccc1]

HPLC RT 4.070 min (Method A) ESIMS [M+1]$^+$ 336, white residue

1H NMR (400 MHz, DMSO-d$_6$) δ ppm 8.85 (d, J=12.92 Hz, 2H) 8.71 (d, J=8.28 Hz, 1H) 7.38-7.43 (m, 2H) 7.32 (t, J=7.59 Hz, 2H) 7.22 (d, J=7.28 Hz, 1H) 5.23 (m, 1H) 1.48 (d, J=6.90 Hz, 3H)

Example 13

(R)—N-(1-phenylpropyl)-5-(5-(trifluoromethyl)-1,2,4-oxadiazol-3-yl)pyrimidin-2-amine

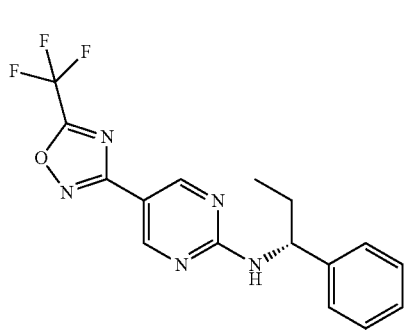 [SMILES: CC[C@@H](Nc1ncc(-c2noc(C(F)(F)F)n2)cn1)c1ccccc1]

HPLC RT 4.227 min (Method A) ESIMS [M+1]$^+$ 350, white-grey residue

1H NMR (400 MHz, DMSO-d$_6$) δ ppm 8.84 (d, J=12.55 Hz, 2H) 8.67-8.73 (m, 1H) 7.40 (d, J=7.15 Hz, 2H) 7.32 (t, J=7.59 Hz, 2H) 7.18-7.25 (m, 1H) 4.89-5.07 (m, 1H) 1.68-1.97 (m, 2H) 0.90 (t, J=7.34 Hz, 3H)

Example 14

N-methyl-N-(2-(pyridin-4-yl)ethyl)-5-(5-(trifluoromethyl)-1,2,4-oxadiazol-3-yl)pyrimidin-2-amine

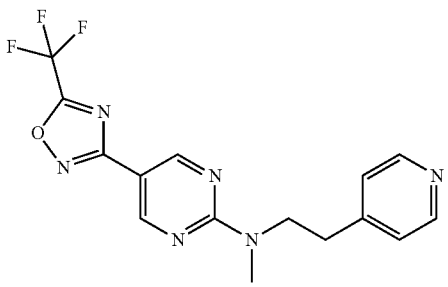 [SMILES: CN(CCc1ccncc1)c1ncc(-c2noc(C(F)(F)F)n2)cn1]

HPLC RT 2.820 min (Method A) ESIMS [M+1]$^+$ 351, white residue

1H NMR (400 MHz, DMSO-d$_6$) δ ppm 8.81-9.04 (m, 2H) 8.68 (d, J=6.27 Hz, 2H) 7.74 (d, J=6.15 Hz, 2H) 4.05 (t, J=7.09 Hz, 2H) 3.19 (s, 3H) 3.11-3.17 (m, 2H)

Example 15

N-(1-(pyridin-4-yl)propyl)-5-(5-(trifluoromethyl)-1,2,4-oxadiazol-3-yl)pyrimidin-2-amine

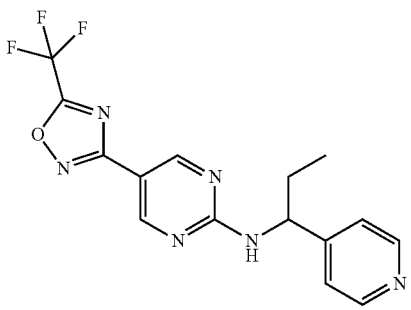 [SMILES: CCC(Nc1ncc(-c2noc(C(F)(F)F)n2)cn1)c1ccncc1]

HPLC RT 2.743 min (Method A) ESIMS [M+1]$^+$ 351, light-yellow residue

1H NMR (400 MHz, DMSO-d$_6$) δ ppm 8.91-8.96 (m, 1H) 8.86-8.91 (m, 1H) 8.78-8.83 (m, 1H) 8.70-8.75 (m, 2H) 7.77-7.83 (m, 2H) 5.08-5.17 (m, 1H) 1.81-1.90 (m, 2H) 0.97 (t, 3H)

Example 16

N-(1-(2-methylpyridin-4-yl)ethyl)-5-(5-trifluoromethyl)-1,2,4-oxadiazol-3-yl)pyrimidin-2-amine

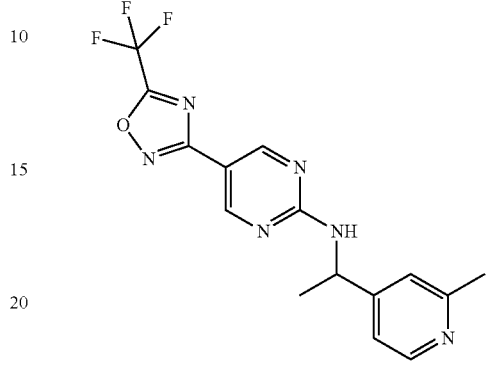

HPLC RT 2.610 min (Method A) ESIMS [M+1]$^+$ 351, opaque-white residue

1H NMR (400 MHz, DMSO-d$_6$) δ ppm 8.80-8.96 (m, 2H) 8.74 (d, J=8.03 Hz, 1H) 8.37 (d, J=5.14 Hz, 1H) 7.26 (s, 1H) 7.19 (d, J=5.14 Hz, 1H) 5.08-5.25 (m, 1H) 2.44 (s, 3H) 1.48 (d, J=7.03 Hz, 3H)

Example 17

N-methyl-N-((2-methylpyridin-4-yl)methyl)-5-(5-(trifluoromethyl)-1,2,4-oxadiazol-3-yl)pyrimidin-2-amine

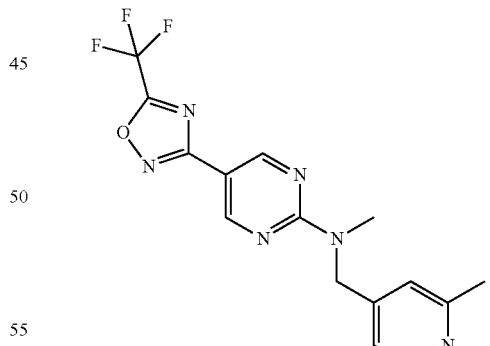

HPLC RT 2.733 min (Method A) ESIMS [M+1]$^+$ 351, colorless residue

1H NMR (400 MHz, METHANOL-d$_4$) δ ppm 8.87-9.15 (m, 2H) 8.61 (d, J=6.15 Hz, 1H) 7.79 (s, 1H) 7.74 (d, J=6.15 Hz, 1H) 5.23 (s, 2H) 3.43 (s, 3H) 2.77 (s, 3H)

The following amines were used in the preparation of Examples 18 to 26

Amine 1:
(R)—N1-benzyl-N1-methylpropane-1,2-diamine

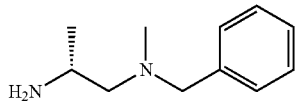

(R)-tert-butyl(1-(benzyl(methyl)amino)-1-oxopropan-2-yl)carbamate

A solution of BOC-D-Ala-OH (3.30, 17.44 mmol) and 2.7 mL (19.5 mmol) triethylamine in 50 mL THF was cooled to −30° C. and treated dropwise with isobutyl chloroformate (2.47 mL (18.8 mmol). The cooling bath was removed and the white suspension was stirred for 3 h at rt. After retooling to 0° C. a solution of benzylmethylamine (2.37 mL, 18.3 mmol) and trietylamine (3.06 mL, 22.0 mmol) in 10 mL THF was slowly added. Stirring overnight at ambient temperature was followed by the addition of 30 mL of sat. sodium bicarbonate solution. Most of the THF was removed under reduced pressure. The resulting aqueous layer was then extracted with diethyl ether, the combined organic layers washed with water and brine. Concentration i.V. afforded the crude product, which was purified by chromatography (Biotage Isolera Four, heptanesethyl acetate 100:0 to 60:40) to give the title product (4.09 g, 14.0 mmol, 80%) in the form of a colorless oil.

$^1$H NMR (600 MHz, DMSO-$d_6$) δ ppm 7.15-7.42 (m, 5H) 7.04 (d, J=7.53 Hz, 1H) 4.54 (d, J=14.49 Hz, 1H) 4.37-4.51 (m, 2H) 2.95 (s, 3H) 1.38 (s, 9H) 1.17 (d, J=1.00 Hz, 3H)

MS (APCI) m/e 293 (M+H)$^+$ RT=1.98 min (Method B)

(R)-tert-butyl(1-(benzyl(methyl)amino)propan-2-yl)carbamate

Lithium aluminum hydride was slowly added to a solution of the amide prepared above (2.9 g, 9.42 mmol) in diethyl ether (30 mL) cooled to 0-5° C. and under an atmosphere of argon. The mixture was stirred at that temperature for 3 h at which time TLC analysis showed that no starting material was left. The reaction was quenched at ice bath temperature by careful subsequent addition of 1 mL water, 1 mL 20% aq. sodium hydroxide solution and another mL of water. The mixture was diluted with ethyl acetate and stirred for 30 mL. Extractive work-up with ethyl acetate/water and concentration i.V. afforded the crude product (2.6 g, 8.41 mmol, 89%) sufficiently pure (ca 90%) to be used directly for the next step.

$^1$H NMR (400 MHz, CDCl$_3$) δ ppm 7.15-7.47 (m, 5H) 4.60-4.84 (m, 1H) 3.76 (s, 2H) 3.37-3.60 (m, 2H) 2.23-2.42 (m, 1H) 2.22 (s, 3H) 1.46 (s, 9H) 1.15 (d, J=1.00 Hz, 3H)

MS (APCI) m/e 279 (M+H)$^+$ RT=1.54 min (Method B)

(R)—N1-benzyl-N1-methylpropane-1,2-diamine

The crude product obtained in the last step (1.0 g, 3.59 mmol) was treated with HCl solution (9 mL, 4 M in dioxane). Hydrolysis was complete after stirring for 3 h at rt. Concentration i.V. left a brown oil which was distributed between ethyl acetate and aq. 2 N sodium hydroxide solution. The crude brown oily product obtained after concentration of the organic layers was purified by chromatography (Biotage Isolera Four, dichloromethane/methanol 100:0 to 90:10) to give the title product (230 mg, 1.29 mmol, 36%) in the form of a yellow oil.

$^1$H NMR (600 MHz, DMSO-$d_6$) δ ppm 7.17-7.36 (m, 5H) 3.34-3.54 (m, 2H) 2.92-3.03 (m, 1H) 2.00-2.19 (m, 5H) 0.91 (d, J=6.21 Hz, 3H)

MS (APCI) m/e 179 (M+H)$^+$ RT=0.29 min (Method B)

The following amines were prepared analogously to Amine 1:

Amine 2: (R)—N,N-dimethylpropane-1,2-diamine

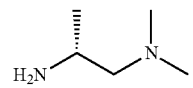

$^1$H NMR (600 MHz, DMSO-$d_6$) δ ppm 8.58 (br. s., 1H) 7.16-7.52 (m, 3H) 3.77 (br. s., 1H) 3.25 (d, J=12.99 Hz, 2H) 2.83 (d, J=1.00 Hz, 6H) 1.31 (d, J=6.40 Hz, 3H)

Amine 3: (R)—N,N-diethylpropane-1,2-diamine

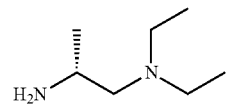

1H NMR (400 MHz, MeOH-$d_4$) δ ppm 3.89-4.03 (m, 1H) 3.35-3.54 (m, 5H) 3.26-3.31 (m, 1H) 1.49 (d, J=6.60 Hz, 3H) 1.42 (t, 6H)

Amine 4:
(R)—N,N-diethyl-3-methylbutane-1,2-diamine

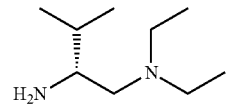

1H NMR (400 MHz, MeOH-$d_4$) δ ppm 3.73-3.80 (m, 1H) 3.37-3.53 (m, 4H) 3.21-3.32 (m, 2H) 2.07-2.20 (m, 1H) 1.43 (d, J=6.36 Hz, 6H) 1.12 (dd, J=6.85, 1.71 Hz, 6H)

Example 18

(R)—N-(1-(dimethylamino)propan-2-yl)-6-(5-(trifluoromethyl)-1,2,4-oxadiazol-3-yl)nicotinamide

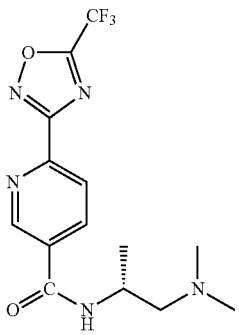 [SMILES: C[C@H](CN(C)C)NC(=O)c1ccc(-c2noc(C(F)(F)F)n2)nc1]

6-(N'-hydroxycarbamimidoyl)nicotinic acid

6-Cyanonicotinic acid (1.50 g, 10.1 mmol) was dissolved in 60 mL EtOH and treated at rt with an excess of hydroxylamine (3.0 mL, 50 mmol, 50% in water). After stirring the yellow solution for 12 h the white suspension was filtered off and washed with petroleum ether.

Yield: 1.75 g (9.66 mmol, 95%) white solid.

$^1$H NMR (600 MHz, DMSO-$d_6$) δ ppm 10.08 (br. s, 1H) 9.01 (d, J=1.13 Hz, 1H) 8.21 (dd, J=8.28, 2.07 Hz, 1H) 7.89 (d, J=8.09 Hz, 1H) 5.91 (br. s, 2H)

MS (APCI) m/e 182 (M+H)$^+$ RT=0.23 min (Method B)

6-(5-(Trifluoromethyl)-1,2,4-oxadiazol-3-yl)nicotinic acid

The product prepared in the step above (800 mg, 4.42 mmol) was dissolved in 22 mL THF and treated with trifluoroacetic anhydride (1.9 mL, 13.5 mmol). The reaction was stirred 14 h at 60° C. The mixture was concentrated i.V. and the residue suspended in ethyl acetate/dichloromethane to give the title compound (830 mg, 3.20 mmol, 73%) as a white solid.

$^1$H NMR (400 MHz, DMSO-$d_6$) δ ppm 13.81 (br. s, 1H) 9.26 (d, J=1.56 Hz, 1H) 8.44-8.61 (m, 1H) 8.29 (d, J=8.20 Hz, 1H)

MS (APCI) m/e 260 (M+H)$^+$ RT=1.74 min (Method B)

(R)—N-(1-(dimethylamino)propan-2-yl)-6-(5-(trifluoromethyl)-1,2,4-oxadiazol-3-yl)nicotinamide The acid (125 mg, 0.482 mmol) prepared in the previous step was dissolved in 1 mL DMF, treated with DIPEA (337 μL, 1.93 mmol) and HATU (257 mg, 0.675 mmol). After stirring for 30 min. (R)—N,N-dimethylpropane-1,2-diamine dihydrochloride was added to the mixture and the vial was stirred for another 2 h. The volatiles were removed and the residue purified by HPLC (SunFire C 18 column, water/acetonitrile 70:30 to 20:80) to afford the product in the form of a yellow foam (85 mg, 0.25 mmol, 51%).

$^1$H NMR (600 MHz, DMSO-$d_6$) δ ppm 9.22 (s, 1H) 9.19 (br. s, 1H) 8.88 (d, J=8.47 Hz, 1H) 8.48 (dd, J=8.19, 1.79 Hz, 1H) 8.34 (d, J=8.09 Hz, 1H) 4.39-4.59 (m, 1H) 3.15-3.31 (m, 2H) 2.74-2.92 (m, 6H) 1.15-1.31 (m, 3H)

MS (APCI) m/e 344 (M+H)$^+$ RT=1.44 min (Method B)

Examples 19 to 23 were prepared in analogy to Example 18.

Example 19

N-(1-(dimethylamino)propan-2-yl)-6-(5-(trifluoromethyl)-1,2,4-oxadiazol-3-yl)nicotinamide

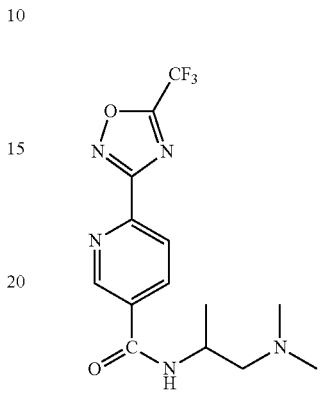

$^1$H NMR (600 MHz, DMSO-$d_6$) δ ppm 9.18 (d, J=2.07 Hz, 1H) 8.62 (d, J=7.72 Hz, 1H) 8.45 (dd, J=8.19, 2.16 Hz, 1H) 8.28 (d, J=8.28 Hz, 1H) 4.10-4.30 (m, 1H) 2.44 (br. s, 1H) 2.20 (br. s, 7H) 1.17 (d, J=6.78 Hz, 3H) MS (APCI) m/e 344 (M+H)$^+$ RT=1.42 min (Method B)

Example 20

(S)—N-(1-hydroxypropan-2-yl)-6-(5-(trifluoromethyl)-1,2,4-oxadiazol-3-yl)nicotinamide

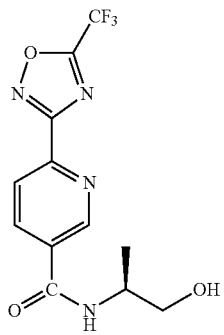 [SMILES: C[C@@H](CO)NC(=O)c1ccc(-c2noc(C(F)(F)F)n2)nc1]

$^1$H NMR (600 MHz, DMSO-$d_6$) δ ppm 9.19 (s, 1H) 8.58 (d, J=8.09 Hz, 1H) 8.46 (d, J=8.09 Hz, 1H) 8.27 (d, J=8.09 Hz, 1H) 4.80 (t, J=5.55 Hz, 1H) 4.06 (dt, J=13.36, 6.49 Hz, 1H) 3.48 (dt, J=10.68, 5.48 Hz, 1H) 3.36-3.43 (m, 1H) 1.16 (d, J=6.59 Hz, 3H)

MS (APCI) m/e 317 (M+H)$^+$ RT=1.60 min (Method B)

Example 21

(R)—N-(1-(benzyl(methyl)amino)propan-2-yl)-6-(5-(trifluoromethyl)-1,2,4-oxadiazol-3-yl)nicotinamide

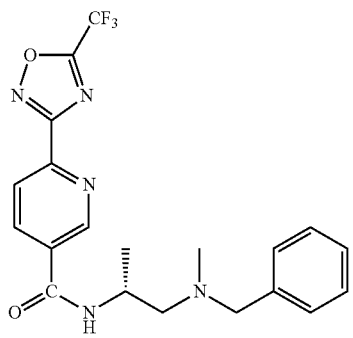 [SMILES: C[C@H](CN(C)Cc1ccccc1)NC(=O)c1ccc(-c2noc(C(F)(F)F)n2)nc1]

$^1$H NMR (600 MHz, DMSO-d$_6$) δ ppm 1.18 (d, J=6.59 Hz, 3H) 2.18 (s, 3H) 2.38 (dd, J=12.14, 7.25 Hz, 1H) 2.44-2.48 (m, 1H) 3.52 (q, J=13.36 Hz, 2H) 4.19-4.39 (m, 1H) 7.17-7.26 (m, 1H) 7.26-7.36 (m, 4H) 8.28 (d, J=8.28 Hz, 1H) 8.44 (dd, J=8.09, 1.88 Hz, 1H) 8.61 (d, J=8.09 Hz, 1H) 9.18 (d, J=1.51 Hz, 1H)

MS (APCI) m/e 420 (M+H)$^+$ RT=1.71 min (Method B)

Example 22

(R)—N-(1-(diethylamino)-3-methylbutan-2-yl)-6-(5-(trifluoromethyl)-1,2,4-oxadiazol-3-yl)nicotinamide

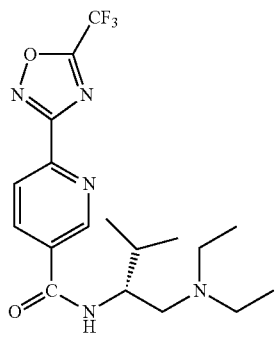 [SMILES: CCN(CC)C[C@H](NC(=O)c1ccc(-c2noc(C(F)(F)F)n2)nc1)C(C)C]

$^1$H NMR (600 MHz, DMSO-d$_6$) δ ppm 9.19 (br. s., 1H) 8.45 (br. d, J=7.50 Hz, 2H) 8.29 (d, J=7.91 Hz, 1H) 3.99-4.19 (m, 1H) 2.49-2.66 (m, 6H) 1.88 (dq, J=13.01, 6.52 Hz, 1H) 0.98-1.17 (m, 6H) 0.93 (dd, J=16.85, 6.68 Hz, 6H)

MS (APCI) m/e 400 (M+H)$^+$ RT=1.70 min (Method B)

Example 23

(R)—N-(1-(diethylamino)propan-2-yl)-6-(5-(trifluoromethyl)-1,2,4-oxadiazol-3-yl)nicotinamide

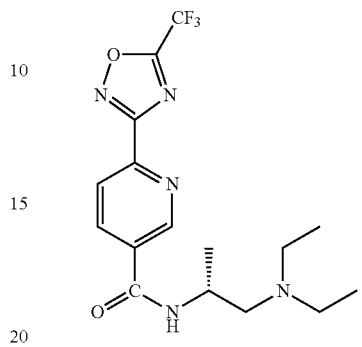

$^1$H NMR (600 MHz, DMSO-d$_6$) δ ppm 9.18 (s, 1H) 8.62 (br. s., 1H) 8.44 (d, J=1.00 Hz, 1H) 8.28 (d, J=8.09 Hz, 1H) 4.09-4.28 (m, 1H) 2.61 (m, 6H) 1.19 (d, J=6.40 Hz, 3H) 1.00 (br. t, 6H)

MS (APCI) m/e 372 (M+H)$^+$ RT=1.56 min (Method B)

Example 24

(R)—N-(1-(dimethylamino)propan-2-yl)-5-(5-(trifluoromethyl)-1,2,4-oxadiazol-3-yl)picolinamide

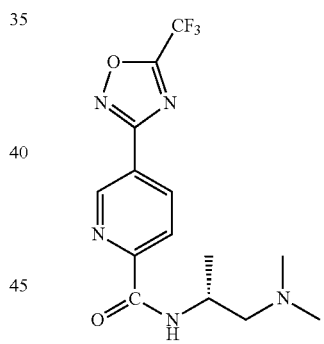

5-(N'-hydroxycarbamimidoyl)picolinic acid

To a solution of 5-cyanopicolinic acid (300 mg, 2.03 mmol) in ethanol (20 mL) was added an excess of hydroxylamine (1.2 mL, 20.3 mmol, 50% in water). The resulting white suspension was stirred for 15 h at rt. Filtration of the solid formed followed by washing with a small amount of water resulted in the crude product (328 mg, 1.81 mmol, 89%) sufficiently pure for the following cyclisation step.

$^1$H NMR (400 MHz, DMSO-d$_6$) δ ppm 8.10 (dd, J=8.20, 2.34 Hz, 2H) 7.89-8.03 (m, 2H) 6.03 (s, 3H)

MS (APCI) m/e 182 (M+H)$^+$ RT=0.19 min (Method B)

5-(5-(trifluoromethyl)-1,2,4-oxadiazol-3-yl)picolinic acid

The intermediate obtained in the previous step (200 mg, 1.10 mmol) was suspended in 11 mL THF, treated with trifluoroacetic anhydride (0.20 mL, 1.43 mmol) and stirred for 60 h at rt. The volatiles were stripped i.V. and the residue taken up into a mixture of water and ethyl acetate. Neutralization of the aqueous layer with sodium bicarbonate solution afforded the slightly brown product (209 mg, 0.071 mmol, 73%) which was used without further purification.

$^1$H NMR (400 MHz, DMSO-d$_6$) δ ppm 9.30 (d, J=1.56 Hz, 1H) 8.60 (dd, J=8.20, 1.95 Hz, 1H) 8.24 (d, J=8.20 Hz, 1H)

MS (APCI) m/e 260 (M+H)$^+$ RT=1.70 min (Method B)

(R)—N-(1-(dimethylamino)propan-2-yl)-5-(5-(trifluoromethyl)-1,2,4-oxadiazol-3-yl)picolinamide A solution of the acid prepared above (110 mg, 0.424 mmol) in 4 mL DMF was treated with HATU (169 mg, 0.446 mmol) and DIPEA (74 µL, 0.424 mmol). After stirring for 5 min. a mixture of the dihydrochlorid salt of (R)—N,N-dimethylpropane-1,2-diamine and 3 eq. of DIPEA (223 µl, 1.28 mmol) in 1 ml DMF were added. The resulting yellow suspension was stirred for 2 h. After work-up with ethyl acetate and water the crude product was purified by chromatography (Biotage Isolera Four, dichloromethane/methanol 100:0 to 90:10) to give the title product (68 mg, 0.192 mmol, 45%) in form of a yellow resin, which crystallized on treatment with diethyl ether.

$^1$H NMR (600 MHz, DMSO-d$_6$) δ ppm 9.26 (dd, J=2.07, 0.75 Hz, 1H) 8.70 (d, J=8.09 Hz, 1H) 8.64 (dd, J=8.19, 2.16 Hz, 1H) 8.26 (dd, J=8.19, 0.66 Hz, 1H) 4.08-4.26 (m, 1H) 2.23 (dd, J=11.76, 5.74 Hz, 2H) 2.16 (s, 6H) 1.15-1.23 (m, 3H)

MS (APCI) m/e 344 (M+H)$^+$ RT=1.56 min (Method B)

Example 25

(R)-3-chloro-N-(1-(dimethylamino)propan-2-yl)-5-(5-(trifluoromethyl)-1,2,4-oxadiazol-3-yl)picolinamide

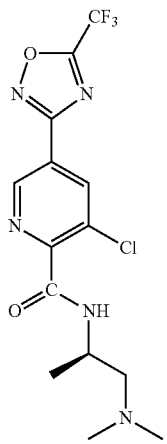 [SMILES: C[C@H](CN(C)C)NC(=O)c1ncc(-c2noc(C(F)(F)F)n2)cc1Cl]

3-Chloro-5-(N'-hydroxycarbamimidoyl)picolinic acid

To a solution of 3-chloro-5-cyanopicolinic acid (240 mg, 1.315 mmol) in ethanol (10 mL) was added an excess of hydroxylamine (0.80 mL, 13.0 mmol, 50% in water). The resulting white suspension was stirred overnight at rt. Filtration of the solid formed followed by washing with small amounts of ethanol, diethyl ether and petroleum ether resulted in the desired product (277 mg, 1.22 mmol, 93%) sufficiently pure for the following cyclisation step.

$^1$H NMR (400 MHz, DMSO-d$_6$) δ ppm 10.00 (br. s, 1H) 8.71 (d, J=1.56 Hz, 1H) 8.08 (d, J=1.95 Hz, 1H) 6.06 (s, 2H)

MS (APCI) m/e 216 (M+H)$^+$ RT=0.18 min (Method B)

3-Chloro-5-(5-(trifluoromethyl)-1,2,4-oxadiazol-3-yl)picolinic acid

3-Chloro-5-(N'-hydroxycarbamimidoyl)picolinic acid (320 mg, 1.41 mmol) was suspended in 10 mL THF, treated with trifluoroacetic anhydride (0.60 mL, 4.23 mmol) and stirred for 2 h at 60° C. in a microwave oven. The mixture was cooled, the volatiles were stripped i.V. and the residual oil crystallized from small amounts of ethyl acetate and diethyl ether. After rinsing with petroleum ether and drying under HV beige crystals were obtained (320 mg, 1.09 mmol, 77%).

$^1$H NMR (600 MHz, DMSO-d$_6$) δ 14.36 (br. s, 1H) 9.17 (s, 1H) 8.63 (s, 1H)

MS (APCI) m/e 250[(M+H)$^+$—CO$_2$] RT=1.87 min (Method B)

(R)-3-chloro-N-(1-(dimethylamino)propan-2-yl)-5-(5-(trifluoromethyl)-1,2,4-oxadiazol-3-yl)picolinamide The acid prepared above (155 mg, 0.528 mmol) in 4 mL THF was treated with HOBT (93 mg, 0.607 mmol) and EDC.HCl (127 mg, 0.660 mmol), followed by the addition of a solution of the dihydrochloride salt of (R)—N,N-dimethylpropane-1,2-diamine (111 mg, 0.634 mmol) and DIPEA (258 µL, 1.48 mmol) in 1 mL of THF. The resulting mixture was stirred for 1 h at 70° C. After work-up with ethyl acetate and water the crude product was purified by chromatography (Biotage Isolera Four, dichloromethane/methanol 100:0 to 95:5) to give the title product (59 mg, 0.156 mmol, 30%) in the form of yellow crystals.

$^1$H NMR (400 MHz, DMSO-d$_6$) δ ppm 9.15 (d, J=1.56 Hz, 1H) 8.59 (m, J=2.00 Hz, 2H) 3.98-4.24 (m, 1H) 3.35 (m, J=2.00 Hz, 1H) 3.24-3.30 (m, 1H) 2.48-2.52 (m, 6H) 1.11-1.20 (m, 3H)

MS (APCI) m/e 378 (M+H)$^+$ RT=1.58 min (Method B)

Example 26

(R)—N-(1-(dimethylamino)propan-2-yl)-2-(5-(trifluoromethyl)-1,2,4-oxadiazol-3-yl)pyrimidine-5-carboxamide

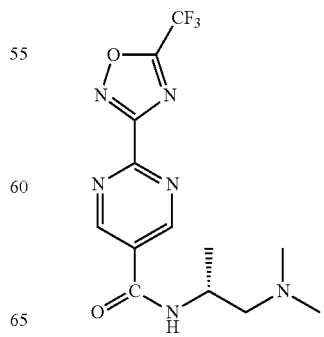

2-(N'-hydroxycarbamimidoyl)pyrimidine-5-carboxylic acid

To a solution of 2-cyanopyrimidine-5-carboxylic acid (4.70 mg, 31.5 mmol) in ethanol (300 mL) was added an excess of hydroxylamine (19 mL, 315 mmol, 50% in water). The resulting white suspension was stirred for 1 h at rt. Filtration of the solid formed followed by washing with methanol resulted in the desired product (5.7 g, 31 mmol, 98%) in pure form.

$^1$H NMR (600 MHz, DMSO-d$_6$) δ ppm 10.29 (br. s, 1H) 9.09 (s, 2H) 6.77-8.55 (m, 1H) 5.88 (br. s, 2H)

MS (APCI) m/e 183 (M+H)$^+$ RT=0.167 min (Method B)

2-(5-(trifluoromethyl)-1,2,4-oxadiazol-3-yl)pyrimidine-5-carboxylic acid

The intermediate prepared above (4.0 g, 22.0 mmol) was suspended in 110 mL THF, treated with 3 equivalents of trifluoroacetic anhydride (9.3 mL, 66 mmol) and stirred for 5 days at 75° C. The mixture was cooled, the volatiles were stripped i.V. and the residue was triturated with diethyl ether. The product was obtained as a beige solid (2.50 g, 9.51 mmol, 43%).

$^1$H NMR (600 MHz, DMSO-d$_6$) δ ppm 9.45 (s, 2H)

MS (ESI) m/e 261 (M+H)$^+$ RT=1.35 min (Method C)

(R)—N-(1-(dimethylamino)propan-2-yl)-2-(5-(trifluoromethyl)-1,2,4-oxadiazol-3-yl)pyrimidine-5-carboxamide The dihydrochloride salt of (R)—N,N-dimethylpropane-1,2-diamine (97 mg, 0.554 mmol) was dissolved in 4.5 mL of THF and treated with HOBT (81 mg, 0.531 mmol), EDC.HCl (111 mg, 0.577 mmol) and DIPEA (322 µL, 1.845 mmol). After stirring for about a minute the acid prepared above (120 mg, 0.461 mmol) was added. Stirring was continued for 1 h at 70° C., then the reaction mixture was cooled and taken up into ethyl acetate and water. The crude product obtained after concentration i. V. was purified by prep. HPLC (Sunfire C 18 column, water/acetonitrile 95:5 to 70:30) to yield the TFA salt of the desired product. Filtration through a SPE PL-HCO$_3$ MP-resin cartouche (Varian) afforded the free base (150 mg, 0.414 mmol, 90%).

$^1$H NMR (400 MHz, DMSO-d$_6$) δ ppm 9.39 (s, 2H) 8.74 (d, J=8.16 Hz, 1H) 4.20 (dt, J=14.21, 7.01 Hz, 1H) 2.43 (dd, J=12.11, 7.59 Hz, 1H) 2.24 (dd, J=12.11, 6.84 Hz, 1H) 2.19 (s, 6H) 1.19 (d, J=6.65 Hz, 3H)

MS (APCI) m/e 345 (M+H)$^+$ RT=1.274 min (Method B)

Example 27

N-benzyl-6-(5-(trifluoromethyl)-1,2,4-oxadiazol-3-yl)pyridin-3-amine

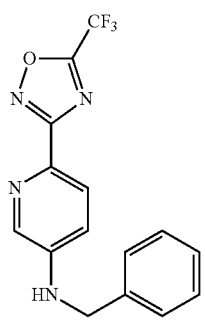 [SMILES: FC(F)(F)c1nc(-c2ccc(NCc3ccccc3)cn2)no1]

5-Amino-N'-hydroxypicolinimidamide

A suspension of aminopicolinonitrile (2.0 g, 16.79 mmol) in ethanol (150 mL) was treated at rt with an excess of hydroxylamine (10.08 mL, 168 mmol, 50% in water). After reducing the slightly red mixture i.V. to a volume of ca. 50 mL diethyl ether was added. The soluble parts were separated from some gooey material and the organic layer was concentrated i.V. The resulting crude material was re-crystallized from Et$_2$O to yield the product in the form of a beige solid (1.48 g, 9.73 mmol, 58%).

$^1$H NMR (600 MHz, DMSO-d$_6$) δ ppm 9.42 (s, 1H) 7.86 (d, J=2.42 Hz, 1H) 7.51 (d, J=8.48 Hz, 1H) 6.91 (dd, J=8.48, 2.62 Hz, 1H) 5.46-5.65 (m, 4H)

MS (APCI) m/e 153 (M+H)$^+$ RT=0.162 min (Method B)

2,2,2-Trifluoro-N-(6-(5-(trifluoromethyl)-1,2,4-oxadiazol-3-yl)pyridin-3-yl)acetamide and

6-(5-(Trifluoromethyl)-1,2,4-oxadiazol-3-yl)pyridin-3-amine

A solution of the material prepared in the step above (703 mg, 4.62 mmol) in THF (40 mL) was treated at 10° C. dropwise with trifluoroacetic anhydride (1.3 mL, 9.24 mmol). The cooling bath was removed and stirring continued overnight. The mixture was distributed between saturated sodium bicarbonate solution and ethyl acetate, the combined organic layers were washed with water and concentrated i.V. The resulting yellow-orange residue was triturated with dichloromethane to give a beige solid containing a mixture of two products. The orange filtrate contained predominantly the trifluoroacetamide, which was purified by chromatography (Biotage Isolera Four, heptanes/ethyl acetate 100:0 to 70:30) to give a white solid (299 mg, 0.91 mmol, 20%).

$^1$H NMR (400 MHz, DMSO-d$_6$) δ ppm 11.79 (s, 1H) 8.94 (s, 1H) 8.25 (d, J=8.59 Hz, 1H) 8.02 (d, J=8.59 Hz, 1H)

MS (APCI) m/e 327 (M+H)$^+$ RT=2.12 min (Method B)

Purification of the beige solid by HPLC (SunFire C 18 column, water/acetonitrile: 97:3 to 70:30) afforded the free aniline (139 mg, 0.60 mmol, 13%) in the form of a slightly pink solid. $^1$H NMR (600 MHz, DMSO-d$_6$) δ ppm 8.08 (d, J=2.62 Hz, 1H) 7.80 (d, J=8.48 Hz, 1H) 7.02 (dd, J=8.48, 2.62 Hz, 1H) 6.22 (s, 1H)

MS (APCI) m/e 231 (M+H)$^+$ RT=1.56 min (Method B)

N-Benzyl-6-(5-(trifluoromethyl)-1,2,4-oxadiazol-3-yl)pyridin-3-amine

A mixture of the amine (150 mg, 0.652 mmol) prepared above, benzyl bromide (100 µl, 0.85 mmol) and cesium carbonate 320 mg (0.98 mmol) in 2.6 mL DMF was heated in a microwave oven at 140° C. Conversion was complete after 30 minutes and the dark suspension was distributed between ethyl acetate and water. The organic layers were washed with brine, dried and concentrated to give a yellow resin. Purification (Biotage Isolera Four, heptanes/ethyl acetate 100:0 to 70:30) afforded a yellow solid (98 mg, 0.208 mmol, 32%).

mp 81-84° C.

$^1$H NMR (400 MHz, DMSO-d$_6$) δ ppm 8.18 (d, J=2.73 Hz, 1H) 7.82 (d, J=8.59 Hz, 1H) 7.31-7.43 (m, 5H) 7.23-

7.31 (m, 1H) 7.03 (dd, J=8.59, 2.73 Hz, 1H) 4.41 (d, J=5.86 Hz, 2H)

MS (APCI) m/e 321 (M+H)+ RT=2.17 min (Method B)

Example 28

N-benzyl-5-(5-(trifluoromethyl)-1,2,4-oxadiazol-3-yl)pyridin-2-amine

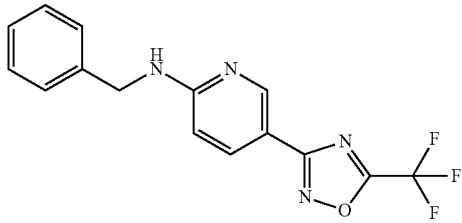 [SMILES: FC(F)(F)c1nc(-c2ccc(NCc3ccccc3)nc2)no1]

6-(Benzylamino)nicotinonitrile

A mixture of aminonicotinonitrile (2.0 g, 16.8 mmol), benzyl bromide (2.6 mL, 21.8 mmol) and cesium carbonate (7.7 g, 23.6 mmol) was stirred in 60 mL DMF for 2 hat 110° C. Concentration i.V. and workup with water/ethyl acetate followed by chromatography (Biotage Isolera Four, heptanes/ethyl acetate 100:0 to 70:30) gave the product as a white solid (161 mg, 0.77 mmol, 4%).

mp 133-134° C.

$^1$H NMR (600 MHz, DMSO-d$_6$) δ ppm 8.40 (d, J=2.07 Hz, 1H) 8.12 (t, J=5.55 Hz, 1H) 7.70 (d, J=8.66 Hz, 1H) 7.28-7.42 (m, 4H) 7.16-7.28 (m, 1H) 6.61 (br. s, 1H) 4.54 (br. s, 2H)

MS (APCI) m/e 210 (M+H)+ RT=1.67 min (Method B)

6-(Benzylamino)-N'-hydroxynicotinimidamide

The product prepared above (150 mg, 0.72 mmol) was dissolved in 10 mL EtOH and treated at rt with an excess of hydroxylamine (0.21 mL, 3.58 mmol, 50% in water). After stirring overnight the mixture was concentrated to give 166 mg of a white crude product which was used in the next step without purification.

$^1$H NMR (400 MHz, DMSO-d$_6$) δ ppm 9.34 (s, 1H) 8.24 (d, J=2.34 Hz, 1H) 7.53-7.70 (m, 1H) 7.14-7.40 (m, 6H) 6.48 (d, J=8.59 Hz, 1H) 5.65 (s, 2H) 4.37-4.55 (m, 2H)

MS (APCI) m/e 243 (M+H)+ RT=0.53 min (Method B)

N-Benzyl-5-(5-(trifluoromethyl)-1,2,4-oxadiazol-3-yl)pyridin-2-amine

The crude hydroxynicotinimidamide (145 mg, 0.57 mmol) prepared in the previous step was dissolved in EtOH and treated with trifluoroacetic anhydride (160 µl, 1.14 mmol) and DIPEA (0.30 mL, 1.71 mmol). The reaction was complete after stirring for 16 h at rt. Extractive workup with ethyl acetate and chromatographic purification (Biotage Isolera Four, heptanes/ethyl acetate 100:0 to 80:30) gave the product in the form of a colorless residue (123 mg, 0.38 mmol, 67%).

$^1$H NMR (400 MHz, DMSO-d$_6$) δ ppm 9.09 (d, J=1.95 Hz, 1H) 8.57 (dd, J=8.59, 2.34 Hz, 1H) 7.79 (d, J=8.59 Hz, 1H) 7.15-7.38 (m, 5H) 518 (s, 2H)

MS (APCI) m/e 321 (M+H)+ RT=1.88 min (Method B)

Example 29

N-(1-phenylethyl)-5-(5-(trifluoromethyl)-1,2,4-oxadiazol-3-yl)pyridin-2-amine

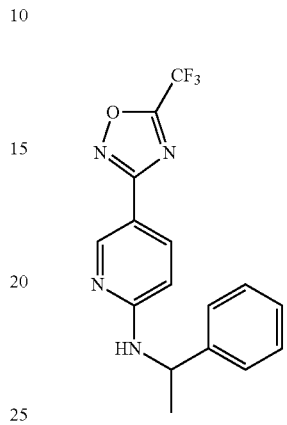

6-Fluoro-N'-hydroxynicotinimidamide

A solution of 6-fluoronicotinonitrile (1.00 g, 8.19 mmol) in EtOH (14 mL) was treated with an excess of hydroxylamine hydrochloride (1.195 g, 17.2 mmol) and 1.81 g (13.1 mmol) of potassium carbonate dissolved in 14 mL of water. A catalytic amount of 8-hydroxyquinone (0.015 g, 0.106 mmol) was added and the resulting solution was stirred at reflux for 4 h. Most of the ethanol was removed under reduced pressure and the aqueous residue was extracted with ethyl acetate. The combined organic layers were washed with brine and concentrated to give the product as an orange solid (1.53 g, 7.43 mmol, 91% yield), which was used without purification for the next step.

$^1$H NMR (400 MHz, DMSO-d$_6$) δ ppm 9.84 (s, 1H) 8.51 (d, J=2.45 Hz, 1H) 8.21 (td, J=8.25, 2.57 Hz, 1H) 7.21 (dd, J=8.56, 2.93 Hz, 1H) 6.01 (s, 2H).

3-(6-Fluoropyridin-3-yl)-5-(trifluoromethyl)-1,2,4-oxadiazole

Trifluoroacetic anhydride (1.58 mL, 11.2 mmol) was added dropwise to a suspension of the crude product prepared in the previous step (1.153 g, 7.43 mmol) dissolved in 25 mL THF. The reaction was complete after stirring for 2 h at rt. THF was removed and the residue was suspended in aq. sodium hydroxide solution and extracted with ethyl acetate. Washing the combined organic layers with brine afforded the title compound after concentration i.V. as a brown, oily solid (1.32 g, 5.66 mmol, 76%) sufficiently pure for the next step.

$^1$H NMR (400 MHz, DMSO-d$_6$) δ ppm 8.94 (d, J=2.69 Hz, 1H) 8.64 (ddd, J=8.62, 7.64, 2.57 Hz, 1H) 7.49 (dd, J=8.56, 2.20 Hz, 1H)

ESIMS m/e 234 (M+H)+ RT=2.10 min (Method D)

N-(1-Phenylethyl)-5-(5-(trifluoromethyl)-1,2,4-oxadiazol-3-yl)pyridin-2-amine

A solution of the fluoride prepared above (50 mg, 0.214 mmol), 1-phenylethanamine (33 µL, 0.257 mmol) and DIPEA (112 µL, 0.643 mmol) in 70 µL n-butanol was stirred in a sealed tube at 100-105° C. for 16 h. The reaction mixture was concentrated and the residue taken up into ethyl acetate/water. The organic layers were concentrated and the crude material was purified by HPLC (SunFire C 18 column, water/acetonitrile 95:5 to 0:100). Filtration through a SPE PL-HCO₃ MP-resin cartouche (Varian) afforded the free base (15.1 mg, 0.452 mmol, 21%).

¹H NMR (400 MHz, DMSO-d₆) δ ppm 8.52-8.63 (m, 1H) 7.83-7.97 (m, 2H) 7.36-7.43 (m, 2H) 7.28-7.36 (m, 2H) 7.17-7.25 (m, 1H) 6.59-6.72 (m, 1H) 5.05-5.27 (m, 1H) 1.47 (d, J=7.09 Hz, 3H).

ESIMS m/e 335 (M+H)⁺ RT=1.97 min (Method D)

Example 30

N-(pyridin-3-ylmethyl)-5-(5-(trifluoromethyl)-1,2,4-oxadiazol-3-yl)pyridin-2-amine

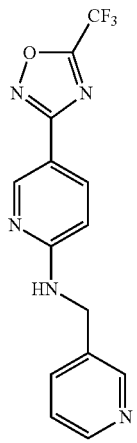 [SMILES: FC(F)(F)c1nc(-c2ccc(NCc3cccnc3)nc2)no1]

6-((Pyridin-3-ylmethyl)amino)nicotinonitrile

Pyridin-3-ylmethanamine (0.40 mL, 3.93 wild) was added to a mixture of 6-chloronicotinonitrile (300 mg, 2.165 mmol), potassium carbonate (748 mg, 5.41 mmol) and a catalytic amount of copper(I) iodide in 5.5 mL DMF. The reaction vial was placed in a microwave oven and stirred for 30 min. at 120° C. DMF was removed i.V. and the residue was distributed between ethyl acetate and water. Evaporation of the organic layers afforded a deep green crude product, which was purified by chromatography (Biotage Isolera Four, heptanes/ethyl acetate 100:0 to 70:30) to give the pure product in the form of pale pink crystals (250 mg, 1.177 mmol, 54%).

¹H NMR (600 MHz, DMSO-d₆) δ ppm 8.53 (s, 1H) 8.42-8.46 (m, 1H) 8.40 (d, J=1.69 Hz, 1H) 8.14 (t, J=5.65 Hz, 1H) 7.61-7.80 (m, 2H) 7.34 (dd, J=7.72, 4.89 Hz, 1H) 6.61 (d, J=8.66 Hz, 1H) 4.56 (d, J=5.27 Hz, 2H)

MS (APCI) m/e 211 (M+H)⁺ RT=0.43 min (Method B)

N'-Hydroxy-6-((pyridin-3-ylmethyl)amino)nicotinimidamide

The intermediate prepared above (197 mg, 0.937 mmol) was dissolved in 8 mL EtOH and treated at rt with an excess of hydroxylamine (0.6 mL, 10 mmol, 50% in water). After stirring the solution for 24 h at rt the white suspension was filtered off and rinsed with diethyl ether. Yield: 140 mg (0.547 mmol, 59%) of a slightly pink powder.

¹H NMR (600 MHz, DMSO-d₆) δ ppm 9.37 (s, 1H) 8.54 (s, 1H) 8.42 (d, J=4.52 Hz, 1H) 8.19-8.29 (m, 1H) 7.70 (d, J=7.91 Hz, 1H) 7.63 (dd, J=8.75, 2.16 Hz, 1H) 7.27-7.37 (m, 2H) 6.50 (d, J=8.66 Hz, 1H) 5.67 (s, 2H) 4.51 (d, J=6.02 Hz, 2H)

MS (APCI) m/e 244 (M+H)⁺ RT=0.20 min (Method B)

N-(Pyridin-3-ylmethyl)-5-(5-(trifluoromethyl)-1,2,4-oxadiazol-3-yl)pyridin-2-amine A solution of the compound prepared in the last step (140 mg, 0.576 mmol) in 5.5 ml THF was treated with 0.3 mL (2.13 mmol) trifluoroacetic anhydride. The reaction mixture was stirred for 1.5 h at rt. The volatiles were evaporated and the residue was purified by chromatography (Biotage Isolera Four, dichloromethane/methanol 100:0 to 95:5) to give the product after washing with diethyl ether as an off-white solid (140 mg, 0.392 mmol, 90%).

¹H NMR (600 MHz, DMSO-d₆) δ ppm 8.74 (br. s, 1H) 8.63 (br. s, 2H) 8.13 (br. s, 2H) 7.99 (d, J=8.09 Hz, 1H) 7.70 (br. s, 1H) 6.76 (d, J=8.47 Hz, 1H) 4.68 (br. s, 2H)

MS (APCI) m/e 322 (M+H)⁺ RT=1.48 min (Method B)

Examples 31 and 32 were prepared in analogy to Example 30

Example 31

N-(pyridin-4-ylmethyl)-5-(5-(trifluoromethyl)-1,2,4-oxadiazol-3-yl)pyridin-2-amine

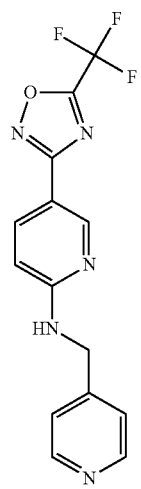

¹H NMR (600 MHz, DMSO-d₆) δ ppm 8.78 (d, J=6.40 Hz, 2H) 8.58 (s, 1H) 8.25 (t, J=5.65 Hz, 1H) 7.96-8.09 (m, 1H) 7.86 (d, J=6.02 Hz, 2H) 6.83 (d, J=8.47 Hz, 1H) 4.83 (d, J=5.65 Hz, 2H)

MS (APCI) m/e 322 (M+H)⁺ RT=1.50 min (Method B)

Example 32

N-((6-methylpyridin-3-yl)methyl)-5-(5-(trifluoromethyl)-1,2,4-oxadiazol-3-yl)pyridin-2-amine

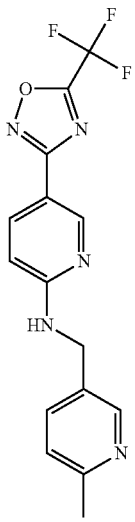

$^1$H NMR (600 MHz, DMSO-d$_6$) δ ppm 8.71 (br. s, 1H) 8.62 (br. s, 1H) 8.31 (d, J=7.15 Hz, 1H) 8.14 (br. s, 1H) 8.00 (d, J=8.09 Hz, 1H) 7.79 (d, J=7.53 Hz, 1H) 6.77 (d, J=8.66 Hz, 1H) 4.56-4.76 (m, 2H) 2.65 (br. s, 3H)

MS (APCI) m/e 336 (M+H)$^+$ RT=1.54 min (Method B)

Example 33

N-benzyl-3-chloro-5-(5-(trifluoromethyl)-1,2,4-oxadiazol-3-yl)pyridin-2-amine

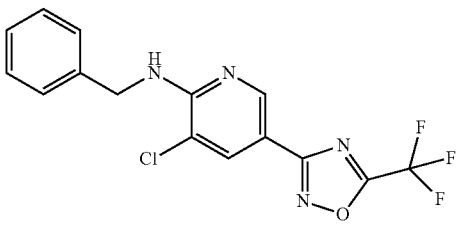 [SMILES: FC(F)(F)c1nc(-c2cnc(NCc3ccccc3)c(Cl)c2)no1]

6-(Benzylamino)-5-chloronicotinonitrile

A mixture of 6-amino-5-chloronicotinonitrile (200 mg, 1.30 mmol), benzyl bromide (200 μL, 1.70 mmol) and cesium carbonate (636 mg, 1.95 mmol) was stirred in 4 mL DMF for 30 minutes in a microwave oven at 140° C. Concentration i.V. and workup with water/ethyl acetate followed by chromatography (Biotage Isolera Four, heptanes/ethyl acetate 100:0 to 70:30) gave the product as a white solid (150 mg, 0.62 mmol, 48%).

mp 112-114° C.

$^1$H NMR (400 MHz, DMSO-d$_6$) δ ppm 8.39 (d, J=1.88 Hz, 1H) 8.17 (t, J=6.15 Hz, 1H) 8.11 (d, J=2.01 Hz, 1H) 7.17-7.33 (m, 5H) 4.65 (d, J=6.27 Hz, 2H)

MS (APCI) m/e 244, 246 (M+H)$^+$ RT=2.15 min (Method B)

6-(Benzylamino)-5-chloro-N'-hydroxynicotinimidamide

The product prepared above (67 mg, 0.275 mmol) was dissolved in 7 mL EtOH and treated at rt with an excess of hydroxylamine (81 μL, 1.37 mmol, 50% in water). After stirring for 18 h the mixture was concentrated to give 75 mg of a colorless oil which was used in the next step without purification.

$^1$H NMR (400 MHz, DMSO-d$_6$) δ ppm 9.51 (s, 1H) 8.23 (d, J=1.95 Hz, 1H) 7.82 (d, J=1.95 Hz, 1H) 7.06-7.42 (m, 6H) 5.78 (s, 2H) 4.62 (d, J=6.25 Hz, 2H)

MS (APCI) m/e 277, 279 (M+H)$^+$ RT=1.43 min (Method B)

N-Benzyl-3-chloro-5-(5-(trifluoromethyl)-1,2,4-oxadiazol-3-yl)pyridin-2-amine The crude product prepared in the step above (65 mg, 0.223 mmol) was dissolved in 5 mL THF and treated with trifluoroacetic anhydride (63 μl, 0.44 mmol) and DIPEA (117 μL, 0.67 mmol). The reaction was stirred at rt overnight. Extractive workup with ethyl acetate/sat. aq. sodium bicarbonate solution followed by chromatographic purification (Biotage Isolera Four, heptanes/ethyl acetate 100:0 to 80:20) gave the desired product in the form of a yellow resin (66 mg, 0.186 mmol, 83% over 2 steps).

$^1$H NMR (400 MHz, DMSO-d$_6$) δ ppm 8.61 (s, 1H) 8.12 (s, 1H) 7.99 (br s, 1H) 7.32-7.22 (m, 5H) 4.70 (br s, 2H)

MS (APCI) m/e 355, 357 (M+H)$^+$ RT=2.52 min (Method B)

Examples 34 to 38 were prepared in analogy to Example 33.

Example 34

(R)-3-chloro-N-(1-phenylethyl)-5-(5-(trifluoromethyl)-1,2,4-oxadiazol-3-yl)pyridin-2-amine

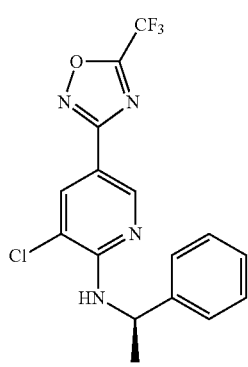 [SMILES: C[C@@H](Nc1ncc(-c2noc(C(F)(F)F)n2)cc1Cl)c1ccccc1]

$^1$H NMR (600 MHz, DMSO-d$_6$) δ ppm 8.52-8.65 (m, 1H) 8.11 (d, J=1.88 Hz, 1H) 7.56 (d, J=8.09 Hz, 1H) 7.42 (d, J=7.53 Hz, 2H) 7.31 (t, J=7.62 Hz, 2H) 7.16-7.24 (m, 1H) 5.44 (quin, J=7.25 Hz, 1H) 1.56 (d, J=7.15 Hz, 3H)

MS (APCI) m/e 369, 371 (M+H)+ RT=2.65 min (Method B)

Example 35

3-chloro-N-(pyridin-4-ylmethyl)-5-(5-(trifluoromethyl)-1,2,4-oxadiazol-3-yl)pyridin-2-amine

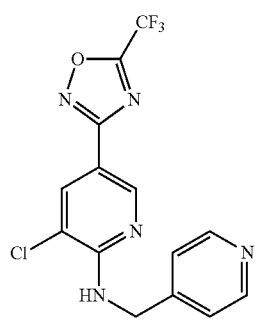 [SMILES: FC(F)(F)c1nc(-c2cnc(NCc3ccncc3)c(Cl)c2)no1]

$^1$H NMR (600 MHz, DMSO-d$_6$) δ 8.57 (d, J=1.69 Hz, 1H) 8.47 (d, J=4.52 Hz, 2H) 8.16 (d, J=1.88 Hz, 1H) 8.10 (t, J=5.93 Hz, 1H) 7.28 (d, J=5.08 Hz, 2H) 4.69 (d, J=6.02 Hz, 2H)

MS (APCI) m/e 356, 358 (M+H)+ RT=1.72 min (Method B)

Example 36

3-chloro-N-(1-(pyridin-4-yl)ethyl)-5-(5-(trifluoromethyl)-1,2,4-oxadiazol-3-yl)pyridin-2-amine

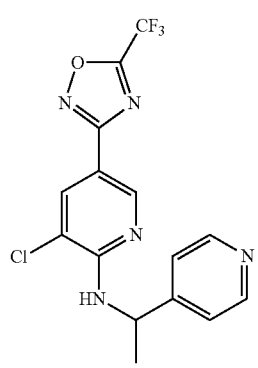 [SMILES: CC(Nc1ncc(-c2noc(C(F)(F)F)n2)cc1Cl)c1ccncc1]

$^1$H NMR (600 MHz, DMSO-d$_6$) δ ppm 8.51-8.69 (m, 1H) 8.48 (d, J=5.65 Hz, 2H) 8.08-8.24 (m, 1H) 7.70 (d, J=7.91 Hz, 1H) 7.39 (d, J=5.65 Hz, 2H) 5.39 (t, J=7.15 Hz, 1H) 1.56 (d, J=7.15 Hz, 3H)

MS (APCI) m/e 370, 372 (M+H)+ RT=1.77 min (Method B)

Example 37

3-chloro-N-(pyridin-3-ylmethyl)-5-(5-(trifluoromethyl)-1,2,4-oxadiazol-3-yl)pyridin-2-amine

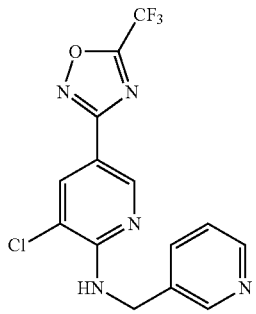 [SMILES: FC(F)(F)c1nc(-c2cnc(NCc3cccnc3)c(Cl)c2)no1]

$^1$H NMR (600 MHz, DMSO-d$_6$) δ ppm 8.61 (d, J=1.88 Hz, 1H) 8.56 (s, 1H) 8.43 (d, J=3.39 Hz, 1H) 8.13 (d, J=1.88 Hz, 1H) 8.08 (t, J=6.02 Hz, 1H) 7.72 (d, J=7.72 Hz, 1H) 7.32 (dd, J=7.72, 4.89 Hz, 1H) 4.69 (d, J=6.02 Hz, 2H)

MS (APCI) m/e 356, 358 (M+H)+ RT=1.72 min (Method B)

Example 38

3-Chloro-N-((6-methylpyridin-3-yl)methyl)-5-(5-(trifluoromethyl)-1,2,4-oxadiazol-3-yl)pyridin-2-amine

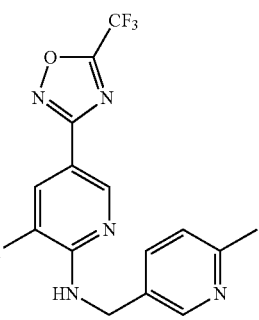

$^1$H NMR (400 MHz, DMSO-d$_6$) δ ppm 8.61 (br. s, 1H) 8.43 (br. s, 1H) 8.12 (br. s, 1H) 8.03 (br. s, 1H) 7.61 (br. s, 1H) 7.09-7.27 (m, 1H) 4.64 (br. s, 2H) 2.41 (br. s, 3H)

MS (APCI) m/e 370, 372 (M+H)+ RT=1.81 min (Method B)

Example 39

3-chloro-N-(pyridin-2-ylmethyl)-5-(5-(trifluoromethyl)-1,2,4-oxadiazol-3-yl)pyridin-2-amine

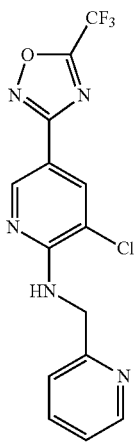 [SMILES: FC(F)(F)c1nc(-c2cnc(NCc3ccccn3)c(Cl)c2)no1]

5-Chloro-6-((pyridin-2-ylmethyl)amino)nicotinonitrile

Catalytic amounts of palladium(II)acetate (7.8 mg, 0.035 mmol) and racemic BINAP (23 mg, 0.035 mmol) were added to degassed toluene (5 mL). After stirring for 5 minutes at it 5,6-dichloronicotinonitrile (200 mg, 1.156 mmol) and 2-picoloylamine (166 µL, 1.619 mmol) were added. Stirring was continued for 10 minutes at rt, then potassium carbonate (811 mg, 5.78 mmol) was added and the temperature was raised to 100° C. for 12 h. The resulting dark suspension was concentrated i.V. and the crude material was purified by chromatography (Biotage Isolera Four, heptanes/ethyl acetate 100:0 to 60:40) to give the desired product as a yellow foam (115 mg, 0.47 mmol, 41%).

$^1$H NMR (400 MHz, DMSO-$d_6$) δ ppm 8.51 (d, J=4.69 Hz, 1H) 8.39 (d, J=1.95 Hz, 1H) 8.07-8.21 (m, 2H) 7.67-7.80 (m, 1H) 7.25 (t, J=7.22 Hz, 2H) 4.74 (d, J=5.86 Hz, 2H)

MS (APCI) m/e 245 (M+H)$^+$ RT=0.80 min (Method B)

5-Chloro-N'-hydroxy-6-((pyridin-2-ylmethyl)amino)nicotinimidamide

The nitrile prepared above (100 mg, 0.409 mmol) was dissolved in 2 mL EtOH and treated at rt with an excess of hydroxylamine (61 µL, 2.04 mmol, 50% in water). After stirring the yellow solution for 12 h the volatiles were stripped off to leave a white solid (100 mg, 0.360 mmol, 88%), which was used in the next step without purification.

$^1$H NMR (400 MHz, DMSO-$d_6$) δ ppm 9.51 (s, 1H) 8.51 (d, J=4.30 Hz, 1H) 8.22 (d, J=1.95 Hz, 1H) 7.84 (d, J=1.95 Hz, 1H) 7.65-7.77 (m, 1H) 7.35 (t, J=5.66 Hz, 1H) 7.16-7.29 (m, 2H) 5.78 (s, 2H) 4.69 (d, J=5.47 Hz, 2H)

MS (APCI) m/e 356 (M+H)$^+$ RT=1.75 min (Method B)

3-Chloro-N-(pyridin-2-ylmethyl)-5-(5-(trifluoromethyl)-1,2,4-oxadiazol-3-yl)pyridin-2-amine The compound prepared in the previous step (100 mg, 0.36 mmol) was dissolved in 2 mL THF and treated with trifluoroacetic anhydride (70 µL, 1.08 mmol). The vial was placed in a microwave oven and stirred for 12 h at rt. Work-up with ethyl acetate, water and bicarbonate solution afforded after concentration of the organic layers i.V. the crude product, which was purified by chromatography (Biotage Isolera Four, heptanes/ethyl acetate 100:0 to 65:35) to give the title compound as a white solid (15 mg, 0.042 mmol, 12% over 2 steps).

$^1$H NMR (600 MHz, DMSO-$d_6$) δ ppm 8.60 (d, J=1.69 Hz, 1H) 8.52 (d, J=4.14 Hz, 1H) 8.17 (d, J=1.69 Hz, 1H) 8.00 (br. s., 1H) 7.74 (s, 1H) 7.23-7.31 (m, 2H) 4.78 (d, J=5.46 Hz, 2H)

MS (APCI) m/e 356 (M+H)$^+$ RT=1.75 min (Method B)

Example 40

N-benzyl-6-(5-(trifluoromethyl)-1,2,4-oxadiazol-3-yl)pyridazin-3-amine

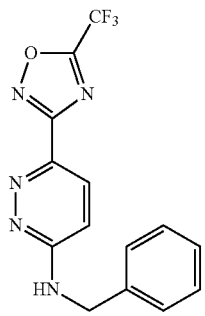 [SMILES: FC(F)(F)c1nc(-c2ccc(NCc3ccccc3)nn2)no1]

3-Chloro-6-iodopyridazine

Dichloropyridazine (5.0 g, 32.9 mmol) was dissolved in 24 mL 47% hydriodic acid. Sodium iodide (6.4 g, 42.8 mmol) was added and the mixture was stirred at 40° C. for 24 h. The thick yellow suspension was cooled and poured onto a mixture of crushed ice (100 g) and conc. sodium hydroxide solution (30 mL). The product was extracted with dichloromethane and the organic layers were concentrated i.V. The residue was taken up into a small amount of diethyl ether. The title compound could be crystallized by the addition of petroleum ether. Yield: 6.50 g (27.0 mmol, 82%).

$^1$H NMR (400 MHz, DMSO-$d_6$) δ ppm 8.21 (d, J=8.98 Hz, 1H) 7.68 (d, J=8.98 Hz, 1H)

MS (APCI) m/e 241, 243 (M+H)$^+$)$^+$ RT=1.02 min (Method B)

6-Chloropyridazine-3-carbonitrile

3-Chloro-6-iodopyridazine (2.75 g, 11.44 mmol) was dissolved in 15 mL acetonitrile and treated with copper(I) cyanide (2.05 g, 22.88 mmol). The mixture was heated in a microwave oven at 160° C. for 30 minutes. The black reaction mixture was added to 100 mL dichloromethane and filtered through Hyflo. Concentration of the organic phase and purification by chromatography (Biotage Isolera Four, heptanes/dichloromethane 100:0 to 30:70) afforded the product as a white solid (1.21 g, 8.67 mmol, 76%).

$^1$H NMR (400 MHz, DMSO-$d_6$) δ ppm 8.46 (d, J=8.98 Hz, 1H) 8.28 (d, J=8.98 Hz, 1H)

MS (APCI) m/e 138, 140 (M+H)$^+$ RT=0.58 min (Method B)

6-(Benzylamino)pyridazine-3-carbonitrile

6-Chloropyridazine-3-carbonitrile (0.72 g, 5.16 mmol) was taken up into 17 mL acetonitrile and benzyl bromide (0.75 mL, 6.86 mmol) and DIPEA (1.8 mL, 10.3 mmol) were added. The mixture was heated in a microwave oven for 30 minutes at 20° C. Workup of the slightly orange solution with water/ethyl acetate afforded an orange solid which was purified by chromatography (Biotage Isolera Four, heptanes/ethyl acetate 100:0 to 60:40) afforded the product as a white solid (640 mg, 4.00 mmol, 77%).

$^1$H NMR (400 MHz, DMSO-$d_6$) δ ppm 8.32 (br. s, 1H) 7.73 (d, J=9.37 Hz, 1H) 7.30-7.43 (m, 4H) 7.22-7.30 (m, 1H) 6.94 (d, J=9.37 Hz, 1H) 4.65 (br. s, 2H)

MS (APCI) m/e 211 (M+H)$^+$ RT=1.77 min (Method B)

6-(Benzylamino)-N'-hydroxypyridazine-3-carboximidamide 6-(Benzylamino)pyridazine-3-carbonitrile (340 mg, 1.62 mmol) was dissolved in 15 mL EtOH and treated at rt with an excess of hydroxylamine (1.0 mL, 17 mmol, 50% in water). Stirring the solution at rt gradually led to a white suspension. Conversion was complete after 5 h. The white suspension was filtered off and dried i.V. Yield: 335 mg (1.35 mmol, 83%) of a white solid.

$^1$H NMR (600 MHz, DMSO-$d_6$) δ ppm 9.83 (s, 1H) 7.66 (t, J=5.45 Hz, 1H) 7.61 (d, J=9.49 Hz, 1H) 7.29-7.38 (m, 4H) 7.21-7.27 (m, 1H) 6.87 (d, J=9.49 Hz, 1H) 5.81 (br. s, 2H) 4.59 (d, J=5.85 Hz, 2H)

MS (APCI) m/e 244 (M+H)$^+$ RT=0.85 min (Method B)

N-Benzyl-6-(5-(trifluoromethyl)-1,2,4-oxadiazol-3-yl)pyridazin-3-amine

The product prepared in the step above (200 mg, 0.82 mmol) was dissolved in 4 mL pyridine and treated with trifluoroacetic anhydride (0.7 mL, 5.0 mmol) which resulted in a vigorous reaction. The mixture was stirred for 30 minutes in a microwave oven at 90° C., followed by work-up with water/sat. sodium bicarbonate solution and ethyl acetate. The combined organic layers were washed with water and brine. The crude product was purified by chromatography (Biotage Isolera Four, heptanes/ethyl acetate 100:0 to 70:30) to give the desired product in the form of a white solid (78 mg, 0.243 mmol, 30%).

$^1$H NMR (600 MHz, DMSO-$d_6$) δ ppm 8.17 (br. s, 1H) 7.89 (d, J=9.41 Hz, 1H) 7.37-7.42 (m, 2H) 7.32-7.37 (m, 2H) 7.24-7.29 (m, 1H) 7.03 (d, J=9.41 Hz, 1H) 4.64-4.74 (m, 2H MS (APCI) m/e 322 (M+H)$^+$ RT=1.87 min (Method B)

Examples 41 to 43 were prepared in analogy to Example 40.

Example 41

(R)—N-(1-Phenylethyl)-2-(5-(trifluoromethyl)-1,2,4-oxadiazol-3-yl)pyrimidin-5-amine

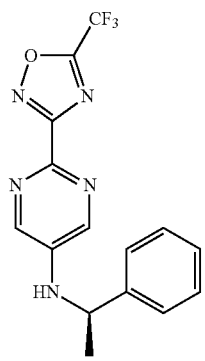 [SMILES: C[C@@H](Nc1cnc(-c2noc(C(F)(F)F)n2)nc1)c1ccccc1]

$^1$H NMR (400 MHz, DMSO-$d_6$) δ ppm 8.48 (d, J=8.91 Hz, 1H) 7.83 (d, J=8.91 Hz, 1H) 7.26-7.38 (m, 5H) 5.91 (q, J=6.94 Hz, 1H) 1.54-1.72 (m, 3H)

MS (APCI) m/e 336 (M+H)$^+$ RT=2.37 min (Method B)

Example 42

(S)—N-(1-Phenylethyl)-2-(5-(trifluoromethyl)-1,2,4-oxadiazol-3-yl)pyrimidin-5-amine

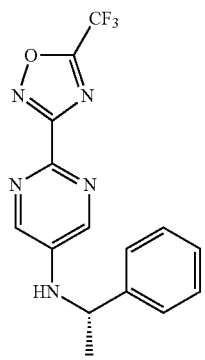 [SMILES: C[C@H](Nc1cnc(-c2noc(C(F)(F)F)n2)nc1)c1ccccc1]

$^1$H NMR (400 MHz, DMSO-$d_6$) δ ppm 8.48 (d, J=8.91 Hz, 1H) 7.83 (d, J=8.91 Hz, 1H) 7.26-7.38 (m, 5H) 5.91 (q, J=6.94 Hz, 1H) 1.54-1.72 (m, 3H)

MS (APCI) m/e 336 (M+H)$^+$ RT=2.35 min (Method B)

Example 43

N-(Pyridin-4-ylmethyl)-2-(5-(trifluoromethyl)-1,2,4-oxadiazol-3-yl)pyrimidin-5-amine (TFA salt)

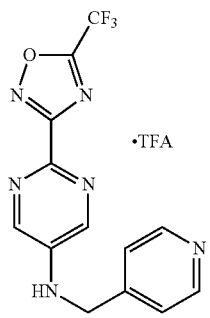 [SMILES: FC(F)(F)c1nc(-c2ncc(NCc3ccncc3)cn2)no1]

$^1$H NMR (600 MHz, DMSO-d$_6$) δ ppm 8.74 (d, J=4.89 Hz, 2H) 8.41 (br. s, 1H) 7.92-8.03 (m, 1H) 7.79 (d, J=5.08 Hz, 2H) 7.17 (d, J=9.22 Hz, 1H) 4.90 (d, J=5.46 Hz, 2H)
MS (APCI) m/e 323 (M+H)$^+$ RT=1.34 min (Method B)

Example 44

(R)—N-(Pyridin-4-yl)ethyl)-5-(5-trifluoromethyl-1,2,4-oxadiazol-3-yl)pyridin-2-amine

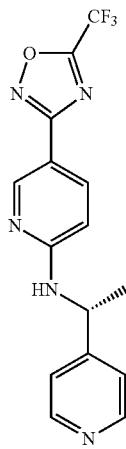 [SMILES: C[C@@H](Nc1ccc(-c2noc(C(F)(F)F)n2)cn1)c1ccncc1]

(R)-6-((1-(pyridin-4-yl)ethyl)amino)nicotinonitrile (R)-1-(Pyridin-4-yl)ethanamine (500 mg, 2.56 mmol) was added to a mixture of 6-chloronicotinonitrile (300 mg, 2.165 mmol), potassium carbonate (1.20 g, 8.7 mmol) and a catalytic amount of copper(I) iodide (25 mg. 0.13 mmol) in 10 mL DMF. The reaction vial was placed in a microwave oven and stirred for 18 h at 120° C. Reaction control of the red suspension showed complete turnover. The mixture was cooled, DMF removed i.V. and the residue was distributed between ethyl acetate and water. Evaporation of the organic layers afforded the crude product, which was purified by chromatography (Biotage Isolera Four, heptanes/ethyl acetate 100:0 to 70:30) to give the pure product in the form of a red-brown solid (129 mg, 0.575 mmol, 27%).

$^1$H NMR (400 MHz, DMSO-d$_6$) δ ppm 8.44-8.53 (m, 2H) 8.32 (d, J=1.96 Hz, 1H) 8.14 (d, J=7.34 Hz, 1H) 7.71 (dd, J=8.93, 2.32 Hz, 1H) 7.34 (m, 2H) 6.52-6.73 (br. d., 1H) 5.10 (br. m., 1H) 1.45 (d, J=7.10 Hz, 3H)
MS (APCI) m/e 225 (M+H)$^+$ RT=0.51 min (Method B)

(R)—N'-Hydroxy-6-((1-(pyridin-4-yl)ethyl)amino)nicotinimidamide

The intermediate prepared above (90 mg, 0.36 mmol) was dissolved in 4 mL EtOH and treated at rt with an excess of hydroxylamine (0.22 mL, 3.6 mmol, 50% in water). After stirring the solution overnight at it the solution was concentrated I.V. Yield: 100 mg (0.35 mmol, 99%) of an off-white solid.

$^1$H NMR (600 MHz, DMSO-d$_6$) δ ppm 9.35 (s, 1H) 8.46 (d, J=4.71 Hz, 2H) 8.15 (s, 1H) 7.61 (d, J=8.66 Hz, 1H) 7.30-7.37 (m, 3H) 6.50 (d, J=8.66 Hz, 1H) 5.64 (br. s., 2H) 5.02 (t, J=6.87 Hz, 1H) 1.42 (d, J=6.78 Hz, 3H).
MS (APCI) m/e 258 (M+H)$^+$ RT=0.18 min (Method B)

R)—N-(Pyridin-4-yl)ethyl)-5-(5-trifluoromethyl-1,2,4-oxadiazol-3-yl)pyridin-2-amine A solution of the compound prepared in the last step (40 mg, 0.155 mmol) in 2 ml THF was treated with 110 μL (0.77 mmol) trifluoroacetic anhydride. The reaction mixture was stirred for 18 h at rt. The volatiles were evaporated and the residue was purified by chromatography (Biotage Isolera Four, dichloromethane/methanol 100:0 to 95:5) to give the product after washing with diethyl ether as an off-white solid (140 mg, 0.392 mmol, 90%).

$^1$H NMR (600 MHz, DMSO-d$_6$) δ ppm 8.77 (d, J=6.21 Hz, 2H) 8.51 (s, 1H) 8.19 (d, J=6.59 Hz, 1H) 8.01 (dd, J=8.85, 2.26 Hz, 1H) 7.90 (d, J=6.02 Hz, 2H) 6.81 (d, J=8.28 Hz, 1H) 5.22-5.34 (m, 1H) 1.52 (d, J=6.96 Hz, 3H)
MS (APCI) m/e 336 (M+H)$^+$ RT=1.59 min (Method B)
Example 45 was prepared in analogy to Example 40.

Example 45

(R)—N-(1-(Pyridin-4-yl)ethyl)-6-(5-(trifluoromethyl)-1,2,4-oxadiazol-3-yl)pyridazin-3-amine

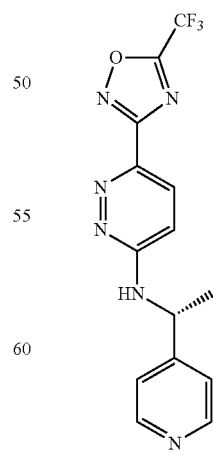

$^1$H NMR (600 MHz, DMSO-d$_6$) δ ppm 8.49 (d, J=5.83 Hz, 2H) 8.19 (br. d., 1H) 7.88 (d, J=9.41 Hz, 1H) 7.39 (d, J=5.83 Hz, 2H) 7.04 (d, J=9.41 Hz, 1H) 5.25 (br. m., 1H) 1.51 (d, J=6.96 Hz, 3H)

MS (APCI) m/e 337 (M+H)+ RT=1.33 min (Method B)

Example 46 was prepared in analogy to Example 26.

Example 46

(R)—N-(1-(benzyl(methyl)amino)propan-2-yl)-6-(5-(trifluoromethyl)-1,2,4-oxadiazol-3-yl)nicotinamide

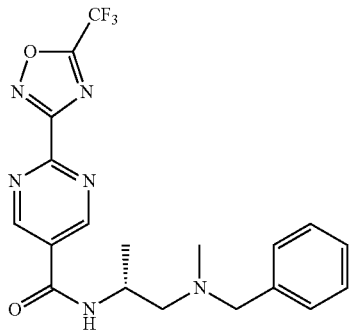 [SMILES: C[C@H](CN(C)Cc1ccccc1)NC(=O)c1cnc(-c2noc(C(F)(F)F)n2)nc1]

$^1$H NMR (600 MHz, DMSO-d$_6$, recorded at 100° C. to avoid seeing signals for the individual rotamers) δ ppm 9.39 (s, 1H) 9.36 (s, 1H) 8.85 (d, J=7.70 Hz, 1H) 7.50 (d, J=3.30 Hz, 2H) 7.42 (dd, J=3.91, 1.59 Hz, 3H) 4.47-4.73 (m, 1H) 4.36 (d, J=13.08 Hz, 1H) 4.22 (d, J=13.08 Hz, 1H) 3.28 (dd, J=12.96, 9.05 Hz, 1H) 3.17 (dd, J=13.00, 9.00 Hz, 1H) 2.75 (s, 3H) 1.31 (d, J=6.60 Hz, 3H MS (APCI) m/e 421 (M+H)+ RT=1.65 min (Method B)

The invention claimed is:

1. A compound of formula (I), or a pharmaceutically acceptable salt thereof,

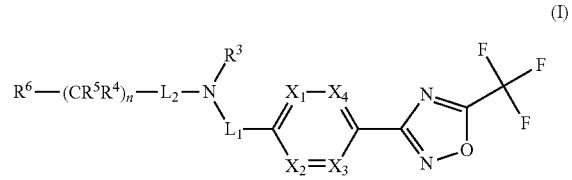

wherein
$X_1$ represents N or $CR^1$;
$X_2$ represents N or $CR^2$;
$X_3$ represents N or CH;
$X_4$ represents N or CH;
and wherein at least one of $X_1$, $X_2$, $X_3$ and $X_4$ is N and not more than two of $X_1$, $X_2$, $X_3$ and $X_4$ are N;
$R^1$ and $R^2$ independently represent hydrogen, chloro or $C_{1-3}$alkyl;
$L_1$ represents a bond or —C(=O)—;
$L_2$ represents a bond;
$R^3$ represents hydrogen or $C_{1-3}$alkyl;
n represents 0, 1, 2 or 3;
$R^4$ and $R^5$ independently on each occurrence represent hydrogen, or $C_{1-3}$alkyl;
$R^6$ represents —$NR^7R^8$, phenyl or a 5- or 6-membered heteroaryl comprising 1, 2, 3 or 4 heteroatoms individually selected from N, O and S and wherein said phenyl or heteroaryl is optionally substituted by 1, 2, 3, 4 or 5 substituents, which may be the same or different, selected from $R^9$;
$R^7$ and $R^8$ independently represent hydrogen, $C_{1-4}$alkyl or benzyl wherein the benzene ring is optionally substituted by 1, 2, 3, 4 or 5 substituents, which may be the same or different, selected from $R^9$; and
$R^9$ represents cyano, amino, halogen, hydroxy, $C_{1-4}$alkyl, $C_{2-4}$alkenyl, $C_{2-4}$alkynyl, halogen$C_{1-4}$alkyl, hydroxy$C_{1-4}$alkyl, $C_{1-4}$alkoxy, $C_{1-4}$alkylamino, di$C_{1-4}$alkylamino, $C_{1-4}$alkylcarbonyl, $C_{1-4}$alkoxycarbonyl, aminocarbonyl, aminocarbonyl$C_{1-4}$alkyl, $C_{1-4}$alkylaminocarbonyl, di$C_{1-4}$alkylaminocarbonyl or $C_{1-4}$alkoxycarbonylamino.

2. A compound according to claim 1, or a pharmaceutically acceptable salt thereof, wherein $R^1$ and $R^2$ independently represent hydrogen or chloro.

3. A compound according to claim 1, or a pharmaceutically acceptable salt thereof, wherein $R^3$ represents hydrogen or methyl.

4. A compound according to claim 1, or a pharmaceutically acceptable salt thereof, wherein n represents 0, 1 or 2.

5. A compound according to claim 1, or a pharmaceutically acceptable salt thereof, wherein $R^4$ and $R^5$ independently on each occurrence represent hydrogen or $C_{1-3}$alkyl.

6. A compound according to claim 1, or a pharmaceutically acceptable salt thereof, wherein $R^6$ represents phenyl or a 6-membered heteroaryl comprising 1, 2, 3 or 4 heteroatoms individually selected from N, O and S and wherein said phenyl or heteroaryl is optionally substituted by 1, 2 or 3 substituents, which may be the same or different, selected from $R^9$.

7. A compound according to claim 1, or a pharmaceutically acceptable salt thereof, wherein $R^6$ represents $NR^7R^8$.

8. A compound according to claim 1, or a pharmaceutically acceptable salt thereof, wherein $R^9$ represents cyano, amino, halogen, hydroxy or $C_{1-3}$alkyl.

9. A compound according to claim 1, which is selected from:
N-methyl-N-(pyridin-4-ylmethyl)-5-(5-(trifluoromethyl)-1,2,4-oxadiazol-3-yl)pyrimidin-2-amine;
N-benzyl-5-(5-(trifluoromethyl)-1,2,4-oxadiazol-3-yl)pyrimidin-2-amine;
N-((2-chloropyridin-4-yl)methyl)-N-methyl-5-(5-(trifluoromethyl)-1,2,4-oxadiazol-3-yl)pyrimidin-2-amine;
N-(pyridin-4-ylmethyl)-5-(5-(trifluoromethyl)-1,2,4-oxadiazol-3-yl)pyrimidin-2-amine;
N-(1-phenylethyl)-5-(5-(trifluoromethyl)-1,2,4-oxadiazol-3-yl)pyrimidin-2-amine;
N-((6-methylpyridin-3-yl)methyl)-5-(5-(trifluoromethyl)-1,2,4-oxadiazol-3-yl)pyrimidin-2-amine;
N-(1-(pyridin-4-yl)ethyl)-5-(5-(trifluoromethyl)-1,2,4-oxadiazol-3-yl)pyrimidin-2-amine;
N-(pyridin-3-ylmethyl)-5-(5-(trifluoromethyl)-1,2,4-oxadiazol-3-yl)pyrimidin-2-amine;
N-((6-methylpyridin-2-yl)methyl)-5-(5-(trifluoromethyl)-1,2,4-oxadiazol-3-yl)pyrimidin-2-amine;
(R)—N-(1-phenylethyl)-5-(5-(trifluoromethyl)-1,2,4-oxadiazol-3-yl)pyrimidin-2-amine;
(R)—N-(1-phenylpropyl)-5-(5-(trifluoromethyl)-1,2,4-oxadiazol-3-yl)pyrimidin-2-amine;
N-methyl-N-(2-(pyridin-4-yl)ethyl)-5-(5-(trifluoromethyl)-1,2,4-oxadiazol-3-yl)pyrimidin-2-amine;
N-(1-(pyridin-4-yl)propyl)-5-(5-(trifluoromethyl)-1,2,4-oxadiazol-3-yl)pyrimidin-2-amine;
N-(1-(2-methylpyridin-4-yl)ethyl)-5-(5-(trifluoromethyl)-1,2,4-oxadiazol-3-yl)pyrimidin-2-amine;

N-methyl-N-((2-methylpyridin-4-yl)methyl)-5-(5-(trifluoromethyl)-1,2,4-oxadiazol-3-yl)pyrimidin-2-amine;
(R)—N-(1-(dimethylamino)propan-2-yl)-6-(5-(trifluoromethyl)-1,2,4-oxadiazol-3-yl)nicotinamide;
N-(1-(dimethylamino)propan-2-yl)-6-(5-(trifluoromethyl)-1,2,4-oxadiazol-3-yl)nicotinamide;
(R)—N-(1-(benzyl(methyl)amino)propan-2-yl)-6-(5-(trifluoromethyl)-1,2,4-oxadiazol-3-yl)nicotinamide;
(R)—N-(1-(diethylamino)-3-methylbutan-2-yl)-6-(5-(trifluoromethyl)-1,2,4-oxadiazol-3-yl)nicotinamide;
(R)—N-(1-(diethylamino)propan-2-yl)-6-(5-(trifluoromethyl)-1,2,4-oxadiazol-3-yl)nicotinamide;
(R)—N-(1-(dimethylamino)propan-2-yl)-5-(5-(trifluoromethyl)-1,2,4-oxadiazol-3-yl)picolinamide;
(R)-3-chloro-N-(1-(dimethylamino)propan-2-yl)-5-(5-(trifluoromethyl)-1,2,4-oxadiazol-3-yl)picolinamide;
(R)—N-(1-(dimethylamino)propan-2-yl)-2-(5-(trifluoromethyl)-1,2,4-oxadiazol-3-yl)pyrimidine-5-carboxamide;
N-benzyl-6-(5-(trifluoromethyl)-1,2,4-oxadiazol-3-yl)pyridin-3-amine;
N-benzyl-5-(5-(trifluoromethyl)-1,2,4-oxadiazol-3-yl)pyridin-2-amine;
N-(1-phenylethyl)-5-(5-(trifluoromethyl)-1,2,4-oxadiazol-3-yl)pyridin-2-amine;
N-(pyridin-3-ylmethyl)-5-(5-(trifluoromethyl)-1,2,4-oxadiazol-3-yl)pyridin-2-amine;
N-((6-methylpyridin-3-yl)methyl)-5-(5-(trifluoromethyl)-1,2,4-oxadiazol-3-yl)pyridin-2-amine;
N-benzyl-3-chloro-5-(5-(trifluoromethyl)-1,2,4-oxadiazol-3-yl)pyridin-2-amine;
(R)-3-chloro-N-(1-phenylethyl)-5-(5-(trifluoromethyl)-1,2,4-oxadiazol-3-yl)pyridin-2-amine;
3-chloro-N-(pyridin-4-ylmethyl)-5-(5-(trifluoromethyl)-1,2,4-oxadiazol-3-yl)pyridin-2-amine;
3-chloro-N-(1-(pyridin-4-yl)ethyl)-5-(5-(trifluoromethyl)-1,2,4-oxadiazol-3-yl)pyridin-2-amine;
3-chloro-N-(pyridin-3-ylmethyl)-5-(5-(trifluoromethyl)-1,2,4-oxadiazol-3-yl)pyridin-2-amine;
3-Chloro-N-((6-methylpyridin-3-yl)methyl)-5-(5-(trifluoromethyl)-1,2,4-oxadiazol-3-yl)pyridin-2-amine;
3-chloro-N-(pyridin-2-ylmethyl)-5-(5-(trifluoromethyl)-1,2,4-oxadiazol-3-yl)pyridin-2-amine;
N-benzyl-6-(5-(trifluoromethyl)-1,2,4-oxadiazol-3-yl)pyridazin-3-amine;
(R)—N-(1-Phenylethyl)-2-(5-(trifluoromethyl)-1,2,4-oxadiazol-3-yl)pyrimidin-5-amine;
(S)—N-(1-Phenylethyl)-2-(5-(trifluoromethyl)-1,2,4-oxadiazol-3-yl)pyrimidin-5-amine;
N-(Pyridin-4-ylmethyl)-2-(5-(trifluoromethyl)-1,2,4-oxadiazol-3-yl)pyrimidin-5-amine;
(R)—N-(Pyridin-4-yl)ethyl)-5-(5-trifluoromethyl-1,2,4-oxadiazol-3-yl)pyridin-2-amine;
(R)—N-(1-(Pyridin-4-yl)ethyl)-6-(5-(trifluoromethyl)-1,2,4-oxadiazol-3-yl)pyridazin-3-amine;
(R)—N-(1-(benzyl(methyl)amino)propan-2-yl)-6-(5-(trifluoromethyl)-1,2,4-oxadiazol-3-yl)nicotinamide;
or a pharmaceutically acceptable salt thereof.

10. A pharmaceutical composition comprising a compound according to claim 1, or a pharmaceutically acceptable salt thereof, as active pharmaceutical ingredient in association with at least one pharmaceutically acceptable carrier or diluent.

11. A method for the treatment of neurodegeneration, or metabolic syndrome, in a subject in need of such treatment, comprising administering to such subject an effective amount of a compound according to claim 1 or a pharmaceutically acceptable salt thereof.

12. A method for the treatment of muscle atrophy, in a subject in need of such treatment, comprising administering to such subject an effective amount of a compound according to claim 1 or a pharmaceutically acceptable salt thereof.

13. The compound N-(pyridine-4-ylmethyl)-5-(5-(trifluoromethyl)-1,2,4-oxadiazol-3-yl)pyridin-2-amine, or a pharmaceutically acceptable salt thereof, having the following structural formula

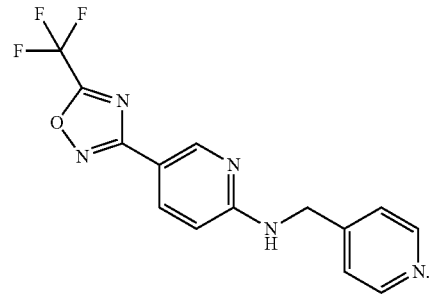 [SMILES: FC(F)(F)c1nc(-c2ccc(NCc3ccncc3)nc2)no1]

* * * * *